(12) United States Patent
Wormser

(10) Patent No.: US 8,765,679 B2
(45) Date of Patent: Jul. 1, 2014

(54) **EXTRACT AND PEPTIDES DERIVED FROM *ORYZA SATIVA* JAPONICA GROUP AND USES THEREOF**

(75) Inventor: Uri Wormser, Jerusalem (IL)

(73) Assignee: Yissum Research Development Company of The Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 13/636,730

(22) PCT Filed: Jun. 29, 2010

(86) PCT No.: PCT/IL2010/000521
§ 371 (c)(1),
(2), (4) Date: Sep. 24, 2012

(87) PCT Pub. No.: WO2011/128884
PCT Pub. Date: Oct. 20, 2011

(65) Prior Publication Data
US 2013/0184219 A1    Jul. 18, 2013

Related U.S. Application Data

(60) Provisional application No. 61/322,857, filed on Apr. 11, 2010.

(51) Int. Cl.
*A61K 38/00* (2006.01)
*C07K 7/06* (2006.01)
(52) U.S. Cl.
USPC ........................................ 514/17.9; 530/326
(58) Field of Classification Search
None
See application file for complete search history.

(56) References Cited

U.S. PATENT DOCUMENTS

| | | |
|---|---|---|
| 2004/0123343 A1 | 6/2004 | La Rosa et al. |
| 2005/0064513 A1 | 3/2005 | Haynes et al. |
| 2006/0123505 A1 | 6/2006 | Kikuchi et al. |
| 2008/0114160 A1 | 5/2008 | Boukharov et al. |

FOREIGN PATENT DOCUMENTS

| | | |
|---|---|---|
| WO | WO 03/017920 | 3/2003 |
| WO | WO 2004/003145 | 1/2004 |
| WO | WO 2005/090387 | 9/2005 |

OTHER PUBLICATIONS

'T Hart et al., Modelling of multiple sclerosis: lessons learned in a non-human primate, Oct. 2004, Lancet Neurology 3(10): 588-597.*
Wekerle et al., Animal models of multiple sclerosis, 2006, Drug Discovery Today: Disease Models 3(4):359-367.*
Ransohoff, R. M., Animal models of multiple sclerosis: the good, the bad and the bottom line. Aug. 2012, Nature Neuroscience 15(8):1074-1077.*
Swiss-Port_Q7F1B1. Hypothetical protein OJ1664_D08.103-1(Os07g0211800 protein) (Hypothetical protein OSJNBb0042J07.10-1). Oct. 31, 2006. [Retrieved from the Internet on Mar. 31, 2011: <URL: http://www.ncbi.nlm.nih.gov/protein/Q7F1B1>]; amino acids 217-232.
Shapira et al. Amelioration of experimental autoimmune encephalitis by novel peptides: involvement of T regulatory cells, Journal of Autoimmunity, Aug. 2010, 35(1):98-106.
International Search Report mailed on May 2, 2011 for International PCT Application No. PCT/IL2010/000521.
Databse UniPort [Online], Feb. 10, 2009, "SubName: Full=cDNA clonse: J013035L06, full insert sequence;", XP002710802, retrieved from EBI accession No. UNIPORT: B7EB72, Database accession No. B7EB72.
European Search Report mailed on Aug. 22, 2013, for EP Application No. 10849767.8.
Singhal et al. Experimental Autoimmune Encephalomyelitis Model for Discovery of New Therapy for Multiple Sclerosis, Global Journal of Pharmacology 6 (3): 208-215, 2012.

* cited by examiner

*Primary Examiner* — John Ulm
(74) *Attorney, Agent, or Firm* — Pearl Cohen Zedek Latzer Baratz LLP

(57) ABSTRACT

The invention relates to isolated peptides derived from *Oryza sativa* Japonica Group, pharmaceutical compositions comprising same, and uses thereof for treating, preventing, ameliorating, and/or delaying the onset of inflammatory and/or neuroinflammatory and/or autoimmune diseases or conditions and in particular multiple sclerosis. The invention further relates to extracts from *Oryza sativa* Japonica Group and use thereof as a dietary supplement or in a pharmaceutical composition for treating, preventing, ameliorating, and/or delaying the onset of inflammatory, and/or inflammatory, neuroinflammatory and/or autoimmune diseases or conditions. The peptides and the extract of the invention may be used for treating, ameliorating, and/or delaying the onset or preventing multiple sclerosis.

5 Claims, 12 Drawing Sheets

```
                        SEQUENCE LISTING

<160> NUMBER OF SEQ ID NOS: 34

<210> SEQ ID NO 1
<211> LENGTH: 16
<212> TYPE: PRT
<213> ORGANISM: ORYZA SATIVA JAPONICA

<400> SEQUENCE: 1

Ala Glu Met Ile Asp Leu Ala Ala Lys Met Leu Ser Glu Gly Arg Gly
1               5                   10                  15

<210> SEQ ID NO 2
<211> LENGTH: 5
<212> TYPE: PRT
<213> ORGANISM: ORYZA SATIVA JAPONICA

<400> SEQUENCE: 2

Ala Glu Met Ile Asp
1               5

<210> SEQ ID NO 3
<211> LENGTH: 6
<212> TYPE: PRT
<213> ORGANISM: ORYZA SATIVA JAPONICA

<400> SEQUENCE: 3

Ala Glu Met Ile Asp Leu
1               5

<210> SEQ ID NO 4
<211> LENGTH: 7
<212> TYPE: PRT
<213> ORGANISM: ORYZA SATIVA JAPONICA

<400> SEQUENCE: 4

Ala Glu Met Ile Asp Leu Ala
1               5

<210> SEQ ID NO 5
<211> LENGTH: 8
<212> TYPE: PRT
<213> ORGANISM: ORYZA SATIVA JAPONICA
```

```
<400> SEQUENCE: 5

Ala Glu Met Ile Asp Leu Ala Ala
1               5

<210> SEQ ID NO 6
<211> LENGTH: 9
<212> TYPE: PRT
<213> ORGANISM: ORYZA SATIVA JAPONICA

<400> SEQUENCE: 6

Ala Glu Met Ile Asp Leu Ala Ala Lys
1               5

<210> SEQ ID NO 7
<211> LENGTH: 10
<212> TYPE: PRT
<213> ORGANISM: ORYZA SATIVA JAPONICA

<400> SEQUENCE: 7

Ala Glu Met Ile Asp Leu Ala Ala Lys Met
1               5                   10

<210> SEQ ID NO 8
<211> LENGTH: 11
<212> TYPE: PRT
<213> ORGANISM: ORYZA SATIVA JAPONICA

<400> SEQUENCE: 8

Ala Glu Met Ile Asp Leu Ala Ala Lys Met Leu
1               5                   10

<210> SEQ ID NO 9
<211> LENGTH: 12
<212> TYPE: PRT
<213> ORGANISM: ORYZA SATIVA JAPONICA

<400> SEQUENCE: 9

Ala Glu Met Ile Asp Leu Ala Ala Lys Met Leu Ser
1               5                   10

<210> SEQ ID NO 10
<211> LENGTH: 13
<212> TYPE: PRT
<213> ORGANISM: ORYZA SATIVA JAPONICA

<400> SEQUENCE: 10

Ala Glu Met Ile Asp Leu Ala Ala Lys Met Leu Ser Glu
1               5                   10

<210> SEQ ID NO 11
<211> LENGTH: 14
<212> TYPE: PRT
<213> ORGANISM: ORYZA SATIVA JAPONICA

<400> SEQUENCE: 11

Ala Glu Met Ile Asp Leu Ala Ala Lys Met Leu Ser Glu Gly
1               5                   10

<210> SEQ ID NO 12
<211> LENGTH: 15
<212> TYPE: PRT
<213> ORGANISM: ORYZA SATIVA JAPONICA

<400> SEQUENCE: 12
```

Ala Glu Met Ile Asp Leu Ala Ala Lys Met Leu Ser Glu Gly Arg
1               5                   10                  15

<210> SEQ ID NO 13
<211> LENGTH: 15
<212> TYPE: PRT
<213> ORGANISM: ORYZA SATIVA JAPONICA

<400> SEQUENCE: 13

Glu Met Ile Asp Leu Ala Ala Lys Met Leu Ser Glu Gly Arg Gly
1               5                   10                  15

<210> SEQ ID NO 14
<211> LENGTH: 5
<212> TYPE: PRT
<213> ORGANISM: ORYZA SATIVA JAPONICA

<400> SEQUENCE: 14

Ser Glu Gly Arg Gly
1               5

<210> SEQ ID NO 15
<211> LENGTH: 6
<212> TYPE: PRT
<213> ORGANISM: ORYZA SATIVA JAPONICA

<400> SEQUENCE: 15

Leu Ser Glu Gly Arg Gly
1               5

<210> SEQ ID NO 16
<211> LENGTH: 7
<212> TYPE: PRT
<213> ORGANISM: ORYZA SATIVA JAPONICA

<400> SEQUENCE: 16

Met Leu Ser Glu Gly Arg Gly
1               5

<210> SEQ ID NO 17
<211> LENGTH: 8
<212> TYPE: PRT
<213> ORGANISM: ORYZA SATIVA JAPONICA

<400> SEQUENCE: 17

Lys Met Leu Ser Glu Gly Arg Gly
1               5

<210> SEQ ID NO 18
<211> LENGTH: 9
<212> TYPE: PRT
<213> ORGANISM: ORYZA SATIVA JAPONICA

<400> SEQUENCE: 18

Ala Lys Met Leu Ser Glu Gly Arg Gly
1               5

<210> SEQ ID NO 19
<211> LENGTH: 10
<212> TYPE: PRT
<213> ORGANISM: ORYZA SATIVA JAPONICA

<400> SEQUENCE: 19

Ala Ala Lys Met Leu Ser Glu Gly Arg Gly
1               5                   10

<210> SEQ ID NO 20
<211> LENGTH: 11
<212> TYPE: PRT
<213> ORGANISM: ORYZA SATIVA JAPONICA

<400> SEQUENCE: 20

Leu Ala Ala Lys Met Leu Ser Glu Gly Arg Gly
1               5                   10

<210> SEQ ID NO 21
<211> LENGTH: 12
<212> TYPE: PRT
<213> ORGANISM: ORYZA SATIVA JAPONICA

<400> SEQUENCE: 21

Asp Leu Ala Ala Lys Met Leu Ser Glu Gly Arg Gly
1               5                   10

<210> SEQ ID NO 22
<211> LENGTH: 13
<212> TYPE: PRT
<213> ORGANISM: ORYZA SATIVA JAPONICA

<400> SEQUENCE: 22

Ile Asp Leu Ala Ala Lys Met Leu Ser Glu Gly Arg Gly
1               5                   10

<210> SEQ ID NO 23
<211> LENGTH: 14
<212> TYPE: PRT
<213> ORGANISM: ORYZA SATIVA JAPONICA

<400> SEQUENCE: 23

Met Ile Asp Leu Ala Ala Lys Met Leu Ser Glu Gly Arg Gly
1               5                   10

<210> SEQ ID NO 24
<211> LENGTH: 16
<212> TYPE: PRT
<213> ORGANISM: ORYZA SATIVA JAPONICA

<400> SEQUENCE: 24

Ala Glu Met Ile Asp Leu Ala Ala Lys Leu Ile Ser Glu Gly Arg Gly
1               5                   10                  15

<210> SEQ ID NO 25
<211> LENGTH: 6
<212> TYPE: PRT
<213> ORGANISM: ORYZA SATIVA JAPONICA

<400> SEQUENCE: 25

Met Leu Ser Glu Gly Arg
1               5

<210> SEQ ID NO 26
<211> LENGTH: 7
<212> TYPE: PRT
<213> ORGANISM: ORYZA SATIVA JAPONICA

<400> SEQUENCE: 26

Met Leu Ser Glu Gly Arg Gly
1               5

```
<210> SEQ ID NO 27
<211> LENGTH: 11
<212> TYPE: PRT
<213> ORGANISM: ORYZA SATIVA JAPONICA

<400> SEQUENCE: 27

Leu Ala Ala Lys Met Leu Ser Glu Gly Arg Gly
1               5                   10

<210> SEQ ID NO 28
<211> LENGTH: 12
<212> TYPE: PRT
<213> ORGANISM: ORYZA SATIVA JAPONICA

<400> SEQUENCE: 28

Cys Leu Ala Ala Lys Met Leu Ser Glu Gly Arg Gly
1               5                   10

<210> SEQ ID NO 29
<211> LENGTH: 4
<212> TYPE: PRT
<213> ORGANISM: ORYZA SATIVA JAPONICA

<400> SEQUENCE: 29

Ala Glu Met Ile
1

<210> SEQ ID NO 30
<211> LENGTH: 4
<212> TYPE: PRT
<213> ORGANISM: ORYZA SATIVA JAPONICA

<400> SEQUENCE: 30

Glu Met Ile Asp
1

<210> SEQ ID NO 31
<211> LENGTH: 9
<212> TYPE: PRT
<213> ORGANISM: Homo sapiens

<400> SEQUENCE: 31

Lys Gly His Tyr Ala Glu Arg Val Gly
1               5

<210> SEQ ID NO 32
<211> LENGTH: 9
<212> TYPE: PRT
<213> ORGANISM: ORYZA SATIVA JAPONICA
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 32

Xaa Glu Met Ile Asp Xaa Xaa Xaa Xaa
1               5

<210> SEQ ID NO 33
<211> LENGTH: 4
<212> TYPE: PRT
<213> ORGANISM: ORYZA SATIVA JAPONICA
```

```
<400> SEQUENCE: 33

Leu Ala Ala Lys
1

<210> SEQ ID NO 34
<211> LENGTH: 5
<212> TYPE: PRT
<213> ORGANISM: ORYZA SATIVA JAPONICA

<400> SEQUENCE: 34

Met Leu Ser Glu Gly
1               5
```

EXTRACT AND PEPTIDES DERIVED FROM *ORYZA SATIVA* JAPONICA GROUP AND USES THEREOF

CROSS-REFERENCE TO RELATED APPLICATIONS

This application is a National Phase Application of PCT International Application No. PCT/IL2010/000521, International Filing Date Jun. 29, 2010, entitled "EXTRACT AND PEPTIDES DERIVED FROM *ORYZA SATIVA* JAPONICA GROUP AND USES THEREOF", published on Oct. 20, 2011, as International Publication No. WO 2011/128884, which claims priority from Provisional Patent Application No. 61/322,857, filed on Apr. 11, 2010, both of which are incorporated by reference in their entirety.

FIELD OF INVENTION

The invention relates to isolated peptides derived from *Oryza sativa* Japonica Group, pharmaceutical compositions comprising same, and uses thereof for treating, preventing, ameliorating, and/or delaying the onset of inflammatory and/or neuroinflammatory and/or autoimmune diseases or conditions and in particular multiple sclerosis. The invention further relates to extracts from *Oryza sativa* Japonica Group and use thereof as a dietary supplement or in a pharmaceutical composition for treating, preventing, ameliorating, and/or delaying the onset of inflammatory, and/or inflammatory, neuroinflammatory and/or autoimmune diseases or conditions. The peptides and the extract of the invention may be used for treating, ameliorating, and/or delaying the onset or preventing multiple sclerosis.

BACKGROUND OF THE INVENTION

Multiple sclerosis (MS) is characterized pathologically by scattered areas of inflammation, demyelination, and axonal pathology affecting the brain, optic nerves, and spinal cord. Individual episodes of inflammatory demyelination may be accompanied by clinical symptoms, termed relapses, followed in most cases by clinical recovery; the resulting pattern of relapse-remission is seen early in disease in most patients.

It is widely believed that the clinical manifestations of MS are mediated by immune-initiated inflammatory demyelination and axonal injury. The brain shows hallmarks of an immunopathologic process including perivascular infiltration by lymphocytes and monocytes, class II MHC antigen expression by cells in the lesions, and cytokine and chemokines secretion by activated cells.

Epidemiologic studies suggest both environmental and genetic factors in the pathogenesis of MS. The geographic distribution of the disease suggests environmental factors or perhaps dietary factors. Worldwide prevalence differs according to geography. The prevalence of MS in the northern United States, Canada and northern Europe is at least 100 per 100,000 persons; in certain regions the prevalence of MS exceeds 300 per 100,000 persons, compared with less than 10 per 100,000 persons in Japan and China.

MS produces numerous neurologic symptoms and signs including damage of the optic nerves, pyramidal tracts, posterior columns, cerebellum, and of the central vestibular system of medial longitudinal fasciculus. Older patients develop progressive spastic leg weakness, axial instability, and bladder impairment. Visual symptoms, sensory symptoms and gait or balance disturbances are frequent symptoms in MS.

Pharmacotherapy of MS includes corticosteroids such as methylprednisolone, interferon $\beta$-1a and interferon $\beta$-1b, glatiramer acetate, natalizumab and immunosuppressants such as methotrexate and mitoxantrone. These agents have some beneficial effect on the intensity and frequency of the relapses in some of MS patients. However, their side effects reduce patient's compliance.

International Patent Publication Nos. WO 03/017920 and WO 2005/090387 of the applicant of the present invention have demonstrated the beneficial effect of a 9-mer peptide, designated 3 ml or IIIM1, derived from histone H2A on an experimental model of MS. Both intravenous and oral administrations of the peptide significantly ameliorated the neurological symptoms in the diseased mice. IIIM1 was also shown to be active in other experimental MS systems such as mouse adoptive transfer and rat EAE models.

There is still an unmet need for improved medicaments to treat inflammatory and autoimmune diseases such as, for example, multiple sclerosis.

SUMMARY OF THE INVENTION

The invention provides isolated peptides capable of preventing, reducing or ameliorating tissue damage due to inflammatory/neuroinflammatory processes.

The invention provides isolated peptides capable of preventing, reducing or ameliorating autoimmune diseases and in particular multiple sclerosis.

The present invention further provides isolated peptides that scavenge free radicals. As was shown in Example 6, the peptides of the invention reduced oxidative burst in activated macrophages. The isolated peptides are effective for treating diseases attributable to the release of free radicals.

The present invention is based in part on the finding that injecting to mice a 9-mer peptide, designated IIIM1, derived from human histone H2A resulted in the appearance, in the serum of these mice, of a 16-mer peptide of the amino acid sequence Ala-Glu-Met-Ile-Asp-Leu-Ala-Ala-Lys-Met-Leu-Ser-Glu-Gly-Arg-Gly (SEQ ID NO: 1). This peptide was detected by liquid chromatography-mass spectrometry (LC/MS/MS). Surprisingly, it was found that the 16-mer peptide, designated RA1, corresponds to the amino acid residues 217-232 of *Oryza sativa* Japonica Group (GeneID: 4342712). The RA1 peptide was identified in the serum of mice injected with IIIM1, but was absent in the serum of mice injected with saline only. As exemplified in Example 1, administration of the serum of mice injected with IIIM1, to mice having experimental autoimmune encephalitis (EAE mice) surprisingly reduced significantly the neurological manifestations of EAE in these mice.

It was further unexpectedly found that the isolated RA1 peptide of SEQ ID NO:1 was highly effective in the treatment of EAE mice and that its effect was achieved whether administered orally, intravenously or intraperitoneally. This is exemplified in Example 2 and in the corresponding figures which all show the dramatic beneficial effect on the neurological score of orally, intravenously or intraperitoneally administered RA1 in the EAE mice.

It is was further shown that RA1 peptide of SEQ ID NO:1 was highly effective as a hydroxyl radical scavenger (see Example 6).

It was surprisingly found and exemplified in Examples 7 and 8 that an acidic extraction of *Oryza sativa* Japonica Group brought about the isolation of acid-soluble factors that were highly effective in the treatment of EAE mice. In contrast, water-soluble factors, obtained by aqueous extraction, were found to be totally inactive.

The present invention encompasses fragments of the RA1 peptide as well as analogs and derivatives thereof.

While the principles of the present invention are exemplified herein below in animal models, the peptides and extract of the invention are particularly useful for the prevention, amelioration, delaying the onset or treatment of inflammatory/neuroinflammatory processes and/or autoimmune diseases in humans.

According to a first aspect, the present invention provides an isolated peptide comprising the amino acid sequence AEMIDLAAKMLSEGRG as set forth in SEQ ID NO:1, or a fragment, analog, or derivative thereof, wherein the fragment, analog, or derivative comprises at least three contiguous amino acid residues of SEQ ID NO:1. According to a certain embodiment, the peptide is of the amino acid sequence as set forth in SEQ ID NO:1. According to the principles of the present invention, the fragments, analogs or derivatives have anti-inflammatory, anti neuroinflammatory and/or immunomodulatory activity or a beneficial effect in the treatment, amelioration, prevention or reducing the onset of multiple sclerosis. According to some embodiments, the at least three contiguous amino acid residues of SEQ ID NO:1 are selected from the group consisting of EMI, MID, and AEM.

According to some embodiments, the peptide fragment derived from RA1 comprises at least 4 contiguous amino acid residues of RA1. According to certain embodiments, the at least four contiguous amino acid residues of RA1 are selected from the group consisting of AEMI (SEQ ID NO:29) and EMID (SEQ ID NO:30). Alternatively, the fragment comprises at least 5 contiguous amino acid residues of RA1. According to a certain embodiment, the fragment consists of the amino acid sequence AEMID (SEQ ID NO:2). This fragment is termed RA5 and effective in reducing the neurological score in EAE mice as shown in Example 9. Alternatively, the fragment comprises at least 6, 7, 8, 9, 10, 11, 12, 13, 14, or 15 contiguous amino acid residues of SEQ ID NO:1. According to additional embodiments, the peptide fragment is of the amino acid sequence selected from the group consisting of SEQ ID NOs:2 to 30 and of the RA fragments 1-16 as listed in Tables 1, 2 and 3.

According to additional embodiments, the peptide comprises the amino acid sequence of SEQ ID NO:1 or an analog thereof, further comprising 1, 2, 3, 4, 5, 6, 7, 8, 9, 10, or more amino acid residues at the amino and/or carboxyl terminus of the peptide, with the proviso that the peptide consists of up to about 50 amino acid residues.

According to a further aspect, the present invention provides a pharmaceutical composition or a dietary supplement comprising as an active ingredient an isolated peptide comprising the amino acid sequence AEMIDLAAKMLSEGRG as set forth in SEQ ID NO:1, or a fragment, analog, or derivative thereof, wherein the fragment, analog, or derivative comprises at least three contiguous amino acid residues of SEQ ID NO:1; and a pharmaceutically acceptable carrier. According to a certain embodiment, the pharmaceutical composition or the dietary supplement comprises as an active ingredient the peptide as set forth in SEQ ID NO:1 and a pharmaceutically acceptable carrier or an acceptable carrier, respectively. According to additional embodiments, the pharmaceutical composition comprises as an active ingredient a peptide as set forth in any one of SEQ ID NOs:2 to 30. According to some embodiments, the pharmaceutical composition comprising the peptide of the invention is formulated for parenteral administration. According to additional embodiments, the pharmaceutical composition or the dietary supplement comprising the peptide of the invention is formulated for oral administration.

According to still further aspect, the present invention provides a method for preventing, ameliorating, delaying the onset or treating a disease or condition attributable to inflammation, neuroinflammation or autoimmune conditions comprising administering to the subject in need of such treatment a therapeutically effective amount of a pharmaceutical composition or the dietary supplement described herein.

Due to their anti-inflammatory, anti-neuroinflammatory or immunomodulatory properties, the peptides of the present invention are useful for treating a diverse group of indications associated with an inflammatory, neuroinflammatory or autoimmune mechanism involved in their etiology or pathogenesis. According to some embodiments, the disease or condition may be inflammatory diseases, autoimmune diseases, degenerative neurological diseases, degenerative muscle diseases, wounds, hypersensitivity, infectious diseases, diseases associated with graft transplantation, allergic diseases, musculo-skeletal inflammations, or sepsis.

According to additional embodiments, the inflammatory, neuroinflammatory or autoimmune disease is selected from the group consisting of multiple sclerosis, arthritis including rheumatoid arthritis, inflammatory bowel disease (Crohn's disease), asthma, chronic bronchitis, sepsis, psoriasis or systemic lupus erythematosus (SLE). According to additional embodiments, the degenerative neurological disease is selected from the group consisting of amyotrophic lateral sclerosis, Parkinson's disease or Alzheimer's disease. According to a certain exemplary embodiment, the disease to be treated is multiple sclerosis According to yet further aspect, the present invention provides a method for scavenging free radicals in a subject comprising administering to a subject in need of such treatment a therapeutically effective amount of a pharmaceutical composition comprising an isolated peptide according to the principles of the present invention, and a pharmaceutically acceptable carrier. According to some embodiments, the pharmaceutical composition to be administered for scavenging free radicals in a subject comprises as an active ingredient the peptide of SEQ ID NO:1 and a pharmaceutically acceptable carrier. Preferably, the subject is a human. According to additional embodiments, the pharmaceutical composition to be administered comprises as an active ingredient an isolated peptide as set forth in any one of SEQ ID NOs:2 to 30.

According to some embodiments, the free radicals are reactive oxygen species (ROS) selected from the group consisting of superoxide radicals, hydrogen peroxide, and hydroxyl radicals. According to additional embodiments, the free radicals are carbon tetra chloride radicals. It will be appreciated that the peptides of the present invention are capable of scavenging other toxic radicals as are known in the art.

According to a further aspect, the present invention provides a method for protecting against or treating a disease or condition attributable to free radicals in a subject comprising administering to the subject in need of such treatment a therapeutically effective amount of a pharmaceutical composition comprising an isolated peptide according to the principles of the present invention, and a pharmaceutically acceptable carrier. According to some embodiments, the pharmaceutical composition to be administered for protecting against or treating a disease or condition attributable to free radicals in a subject comprises as an active ingredient the peptide of SEQ ID NO:1 and a pharmaceutically acceptable carrier. Preferably, the subject is a human. According to additional embodiments, the pharmaceutical composition to be administered comprises as an active ingredient an isolated peptide as set forth in any one of SEQ ID NOs:2 to 30.

According to some embodiments, the free radicals are reactive oxygen species selected from the group consisting of superoxide radicals, hydrogen peroxide, and hydroxyl radicals. Preferably, the subject to be treated is a human.

According to other embodiments, the disease or condition attributable to reactive oxygen species to be treated by the pharmaceutical compositions of the invention are selected from the group consisting of neuronal diseases, lung diseases, cardiovascular diseases, and digestive organ diseases.

According to additional embodiments, the disease or condition attributable to free radicals is brain infarction, brain edema, Parkinson's disease, Alzheimer's disease, multiple sclerosis, lung oxygen intoxication, chronic bronchitis, adult respiratory distress syndrome, ischemic diseases (e.g., myocardial infarction and arrhythmia), arteriosclerosis, peptic ulcer, ulcerative colitis, or Crohn's disease. It will be appreciated that biological damages caused by infections can also be treated with the pharmaceutical compositions of the invention.

According to a further aspect, the present invention provides use of the isolated peptides of the invention in preventing, treating, ameliorating, delaying the onset of a disease or condition attributable to inflammatory processes or to autoimmune disease according to the principles of the present invention.

According to still further aspect, the present invention provides use of the isolated peptides of the invention for treating a disease attributable to free radicals according to the principles of the present invention.

According to still further aspect, the isolated peptides and the composition comprising them as described in the invention are suitable for preventing, treating, ameliorating, delaying the onset of a disease or condition attributable to inflammatory/neuroinflammatory processes or to autoimmune disease according to the principles of the present invention.

In some embodiments of the invention, there is provided an isolated peptide consisting of the amino acid sequence SEQ ID NO: 32 wherein the sequence is $X_1EMIDX_2X_3X_4X_5$, wherein $X_1$ is A or nothing; $X_2$ is SEQ ID NO: 33 wherein the sequence is LAAK or nothing wherein if said $X_2$ is nothing, $X_3$, $X_4$ and $X_5$ are nothing; $X_3$ is SEQ ID NO: 34 wherein the sequence is MLSEG or nothing wherein if said $X_3$ is nothing $X_4$ and $X_5$ are nothing; $X_4$ is R or nothing, wherein if said $X_4$ is nothing $X_5$ is nothing; $X_5$ is G or nothing.

In some embodiments of the invention, the isolated peptide comprising the amino acid sequence AEMIDLAAKMLSEGRG as set forth in SEQ ID NO:1 of the invention is suitable for treating, ameliorating, preventing, delaying the onset of multiple sclerosis.

In some embodiments of the invention, a composition which may be an extract, a pharmaceutical composition or a dietary nutrition comprising the isolated peptide that comprises the amino acid sequence AEMIDLAAKMLSEGRG as set forth in SEQ ID NO:1 is provided wherein the composition is suitable for treating, ameliorating, preventing, delaying the onset of multiple sclerosis.

In an embodiment of the invention, there is provided an extract from Oryza sativa Japonica Group, having an amount of a peptide consisting of the amino acid sequence AEMIDLAAKMLSEGRG as set forth in SEQ ID NO:1 or a fragment thereof. In some embodiments the extracts may be enriched by exogenous peptide comprising the amino acid sequence AEMIDLAAKMLSEGRG as set forth in SEQ ID NO:1 so as to provide a therapeutically effective amount.

In some embodiments of the invention, the extract is obtainable by the following steps: (i) heating Oryza sativa Japonica Group in water for a first predetermined period of time; (ii) cooling the Oryza sativa Japonica Group of step (i); (iii) mixing the Oryza sativa Japonica Group of step (ii) with an acid for a second predetermined period of time; (iv) and separating a non-soluble fraction from a soluble fraction. The soluble fraction can be then collected.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
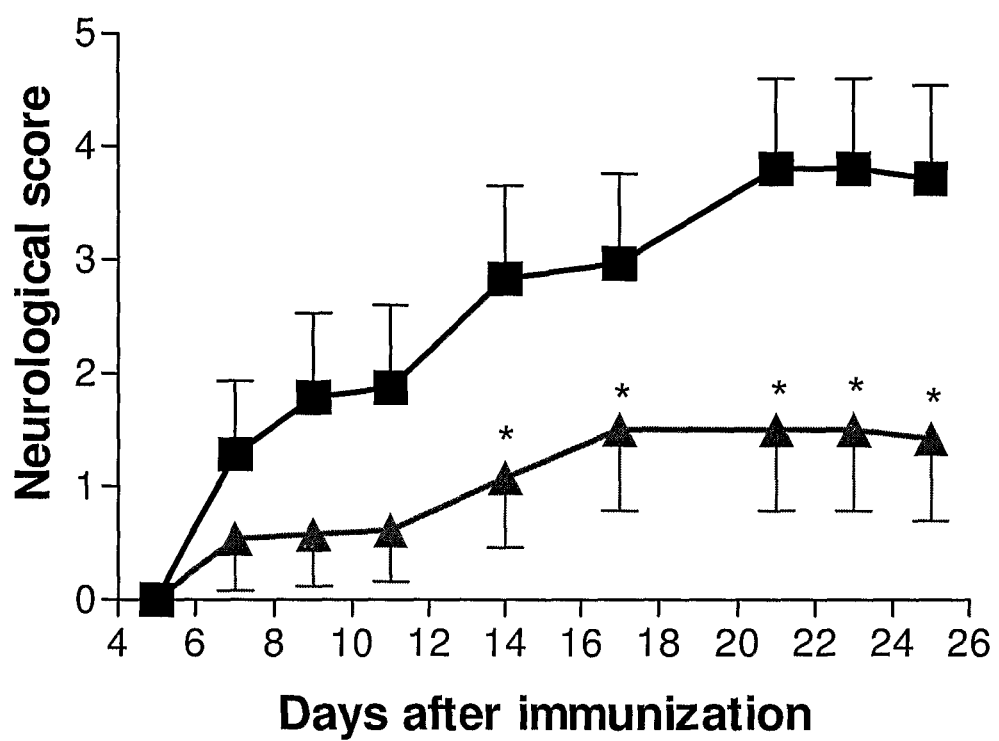
FIG. 1 shows the effect of sera obtained from mice injected with IIIM1 on the neurological manifestation of experimental autoimmune encephalitis (EAE) in mice. Female mice were injected intravenously (i.v.) with IIIM1. Control mice received saline injection. Three days later, sera of each group were obtained and i.v. injected into two groups of naïve mice. Twenty minutes later both groups were immunized with myelin oligodendrocyte glycoprotein (MOG) peptide 35-55 to induce EAE and the neurological score was evaluated.

The present invention provides isolated peptides derived from amino acid residues 217 to 232 of *Oryza Sativa* Japonica group. Particularly, the present invention provides an isolated peptide of the amino acid sequence Ala-Glu-Met-Ile-Asp-Leu-Ala-Ala-Lys-Met-Leu-Ser-Glu-Gly-Arg-Gly (SEQ ID NO: 1) designated herein RA1. The present invention further relates to fragments, analogs, and derivatives of peptide RA1 that are useful for treating or protecting a subject against inflammatory conditions, diseases, autoimmune diseases, or diseases associated with free radicals.

As contemplated herein, the present invention demonstrates that administration of the peptide RA1 to animals reduces the degree of inflammatory processes. The peptide of the present invention is also capable of scavenging oxygen free radicals and hence can prevent or reduce biological damage caused by free oxygen radicals, particularly hydroxyl radicals. The peptides of the present invention are, therefore, useful for treating diseases such as inflammatory, autoimmune, neurological, cardiovascular, and connective tissue diseases.

The present invention also encompasses fragments or analogs of RA1 designated RA2, RA3, RA4, RA5, RA6, RA7, RA8, RA9, RA10, RA11, RA12, RA13, RA14, RA15, and RA16 as listed in Table 1:

TABLE 1

| Designation | SEQ ID NO: | Amino Acid Sequence |
|---|---|---|
| RA1 | 1 | AEMIDLAAKMLSEGRG |
| RA2 | 13 | EMIDLAAKMLSEGRG |
| RA3 | 12 | AEMIDLAAKMLSEGR |
| RA4 | 11 | AEMIDLAAKMLSEG |
| RA5 | 2 | AEMID |
| RA6 | 6 | AEMIDLAAK |
| RA7 | 25 | MLSEGR |
| RA8 | 26 | MLSEGRG |
| RA9 | 27 | LAAKMLSEGRG |
| RA10 | 28 | CLAAKMLSEGRG |
| RA12 | 29 | AEMI |
| RA13 | 30 | EMID |
| RA14 | | EMI |
| RA15 | | MID |
| RA16 | | AEM |
| RA11 | 24 | AEMIDLAAKLISEGRG |

The present invention encompasses the following peptides:

TABLE 2

| RA1 carboxy truncations | |
|---|---|
| Amino Acid Sequence | SEQ ID NO: |
| X-AEMID-Z | 2 |
| X-AEMIDL-Z | 3 |
| X-AEMIDLA-Z | 4 |
| X-AEMIDLAA-Z | 5 |
| X-AEMIDLAAK-Z | 6 |
| X-AEMIDLAAKM-Z | 7 |
| X-AEMIDLAAKML-Z | 8 |
| X-AEMIDLAAKMLS-Z | 9 |
| X-AEMIDLAAKMLSE-Z | 10 |
| X-AEMIDLAAKMLSEG-Z | 11 |
| X-AEMIDLAAKMLSEGR-Z | 12 |
| X-AEMIDLAAKMLSEGRG-Z | 1 |

"X" may represent an amino group; an acetyl group; a 9-fluorenylmethoxy-carbonyl group.
"Z" may represent a carboxyl group; an amido group; a T-butyloxycarbonyl group.

TABLE 3

RA1 amino truncations

| Amino Acid Sequence | SEQ ID NO: |
|---|---|
| X-SEGRG-Z | 14 |
| X-LSEGRG-Z | 15 |
| X-MLSEGRG-Z | 16 |
| X-KMLSEGRG-Z | 17 |
| X-AKMLSEGRG-Z | 18 |
| X-AAKMLSEGRG-Z | 19 |
| X-LAAKMLSEGRG-Z | 20 |
| X-DLAAKMLSEGRG-Z | 21 |
| X-IDLAAKMLSEGRG-Z | 22 |
| X-MIDLAAKMLSEGRG-Z | 23 |
| X-EMIDLAAKMLSEGRG-Z | 13 |

"X" may represent an amino group; an acetyl group; a 9-fluorenylmethoxy-carbonyl group.
"Z" may represent a carboxyl group; an amido group; a T-butyloxycarbonyl group.

The present invention discloses an isolated peptide designated RA1 as set forth in SEQ ID NO: 1 derived from *Oryza sativa* Japonica Group, and fragments, derivatives and analogs thereof.

The term "peptide" as used herein refers to a linear series of natural, non-natural and/or chemically modified amino acid residues connected one to the other by peptide bonds. The amino acid residues are represented throughout the specification and claims by either one or three-letter codes, as is commonly known in the art.

The terms "analog" and "derivative" refer to a peptide comprising at least one altered amino acid residue by an amino acid substitution, addition, deletion, or chemical modification, as compared with the native peptide. Peptide derivatives particularly include amino acid substitutions and/or additions with naturally occurring amino acid residues, and chemical modifications such as, for example, enzymatic modifications, typically present in nature. Peptide analogs particularly include amino acid substitutions and/or additions with non-natural amino acid residues, and chemical modifications which do not occur in nature. Thus, the present invention encompasses both peptide derivatives and analogs of the RA1 peptide as set forth in SEQ ID NO: 1. The analogs and derivatives comprise an amino acid sequence that is at least 70%, at least 80%, or at least 90% identical to the amino acid sequence of RAI of SEQ ID NO:1.

According to the principles of the present invention, the peptide fragments, derivatives derivatives or analogs of RA1 peptide do not include the intact *Oryza sativa* Japonica Group or any known fragments thereof.

The term "isolated" peptide refers to a peptide that is essentially free from contaminating cellular components, such as carbohydrate, lipid, or other proteinaceous impurities associated with the peptide in nature. Typically, a preparation of isolated peptide contains the peptide in a highly purified form, i.e., at least about 80% pure, at least about 90% pure, at least about 95% pure, greater than 95% pure, or greater than 99% pure.

By using "amino acid substitutions", it is meant that functionally equivalent amino acid residues are substituted for residues within the sequence resulting in a silent change. The term "functionally equivalent" means, for example, a group of amino acids having similar polarity, similar charge, or similar hydrophobicity. For example, one or more amino acid residues within the sequence can be substituted by another amino acid of a similar polarity, which acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, a non-conservative substitution can be made in an amino acid that does not contribute to the biological activity of the peptide. Such non-conservative substitutions are also encompassed within the term "amino acid substitution", as used herein. It will be appreciated that the present invention further encompasses peptide RA1 derivatives or analogs, wherein at least one amino acid is substituted by another amino acid to produce a peptide derivative or analog having increased stability or higher half life as compared to RA1 peptide.

The present invention encompasses peptides of which at least one amino acid has been chemically modified. Chemical modifications of amino acid residues include, but are not limited to, amidation, methylation, acetylation, glycosylation, oxidation, reduction, myristylation, sulfation, acylation, ADP-ribosylation, cyclization, hydroxylation, iodination, derivatization by protecting/blocking groups, or any other derivatization method known in the art. Such alterations, which do not destroy, but may improve the biological activity of RA1 peptide, can occur anywhere along the sequence of the peptide, including at the peptide backbone, the amino acid side-chains, and at the amino or carboxyl termini.

The term "fragment" as used herein refers to a portion of a peptide, peptide derivative or peptide analog having an anti-inflammatory or immunomodulatory activity and may have an additional biological activity selected from the group consisting of free radical scavenging activity, metal chelating activity, and metalloproteinase inhibitory activity.

The present invention encompasses peptide hydrates. The term "hydrate" includes, but is not limited to, hemihydrate, monohydrate, dihydrate, trihydrate, and the like.

Peptide RA1 and analogs, derivatives and fragments thereof can be produced by various methods known in the art, including recombinant production or synthetic production. Recombinant production can be achieved by the use of an isolated polynucleotide encoding peptide RA1, or a fragment, derivative or analog thereof, the isolated polynucleotide operably linked to a promoter for the expression of the polynucleotide. Optionally, a signal peptide and a regulator of the promoter are added. The construct comprising the polynucleotide encoding the peptide RA1, or a fragment, derivative or analog thereof, the promoter, and optionally the regulator can be placed in an expression vector, such as a plasmid, virus or phage vector. The vector can be used to transfect or transform a host cell, e.g., a bacterial, yeast, insect, or mammalian cell. The vector can also be introduced into a transgenic animal such as, for example, a transgenic mouse.

Alternatively, the peptide can be produced synthetically. Synthetic production of peptides is well known in the art. The RA1 peptide, derivatives, analogs and/or fragments thereof can be synthesized using standard direct peptide synthesis (see, for example, Bodanszky, 1984, Principles of Peptide Synthesis, Springer-Verlag, Heidelberg), such as via solid-phase synthesis (see, for example, Merrifield, 1963, J. Am. Chem. Soc. 85:2149-2154, the contents of which are hereby incorporated by reference in their entirety). Examples of solid phase peptide synthesis methods include, but are not limited to, the BOC method, which utilizes tert-butyloxycarbonyl as the α-amino protecting group, and the FMOC method, which utilizes 9-fluorenylmethyloxycarbonyl to protect the α-amino of the amino acid residues, both methods are well-known by those of skill in the art.

Alternatively, the peptide derivatives, analogs, and fragments of the present invention can be synthesized using standard solution methods (see, for example, Bodanszky, M., Principles of Peptide Synthesis, Springer-Verlag, 1984, the content of which is hereby incorporated by reference in its entirety).

The peptide derivatives, analogs, and fragments according to the principles of the present invention can also include side chain bond modifications, including but not limited to —$CH_2$—NH—, —$CH_2$—S—, —$CH_2$—S=O, O=C—NH—, —$CH_2$—O—, —$CH_2$—$CH_2$—, S=C—NH—, and —CH=CH—, and backbone modifications such as modified peptide bonds. Peptide bonds (—CO—NH—) within the peptide can be substituted, for example, by N-methylated bonds (—N($CH_3$)-CO—); ester bonds (—C(R)H—C—O—O—C(R)H—N); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides, and amides. The imidazole nitrogen of histidine can be derivatized to form N-im-benzylhistidine.

Also included are those peptide derivatives, which contain one or more naturally occurring amino acid derivatives of the twenty standard amino acid residues. For example: 4-hydroxyproline can be substituted for proline; 5-hydroxylysine can be substituted for lysine; 3-methylhistidine can be substituted for histidine; homoserine can be substituted or serine; and ornithine can be substituted for lysine. The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (MeAla), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide RA1 analogs, which can contain one or more D-isomer forms of the amino acids. Production of retro-inverso D-amino acid peptides where at least one amino acid, and perhaps all amino acids, is D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein.

Included within the scope of the invention are peptide conjugates comprising a RA1 peptide derivative, analog, or fragment thereof joined at its amino or carboxy-terminus or at one of the side chains via a peptide bond to an amino acid sequence of a different protein. Additionally or alternatively, a RA1 peptide derivative, analog, or fragment thereof can be joined to another moiety such as, for example, a fatty acid, a sugar moiety, arginine residues, and any known moiety that facilitate membrane or cell penetration. Conjugates comprising peptides of the invention and a protein can be made by protein synthesis, e.g., by use of a peptide synthesizer, or by ligating the appropriate nucleic acid sequences encoding the desired amino acid sequences to each other by methods known in the art, in the proper coding frame, and expressing the conjugate by methods commonly known in the art.

The person skilled in the art would have no problem in determining which of the peptide analogs, derivatives or fragments falls under the scope of the invention. A peptide derivative, analog, or fragment can be prepared and tested in one of the assays disclosed herein below: assays for anti-inflammatory and immunomodulatory activities and assays for free radical scavenging (see the Examples herein below). A peptide derivative, analog, or fragment which is active in one of these assays or in any assay aimed at evaluating an anti-inflammatory activity as known in the art (see, for example, WO 2005/090387, the content of which is incorporated by reference as if fully set forth herein) falls under the scope of the invention.

According to another aspect, the present invention provides an isolated polynucleotide sequence encoding the RA1 peptide, or a fragment, derivative, analog, or a conjugate thereof, the RA1 peptide, fragment, derivative, analog, or conjugate thereof has anti-inflammatory activity and can have free radical scavenging activity, and/or immunomodulatory activity and/or T cell inhibitory activity.

The term "polynucleotide" means a polymer of deoxyribonucleic acid (DNA), ribonucleic acid (RNA) or a combination thereof, which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a peptide or protein if transcription and translation of mRNA corresponding to that gene produces the peptide or protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the peptide or protein or other product of that gene or cDNA.

One who is skilled in the art will appreciate that more than one polynucleotide may encode any given peptide or protein in view of the degeneracy of the genetic code and the allowance of exceptions to classical base pairing in the third position of the codon, as given by the so-called "Wobble rules." It is intended that the present invention encompass polynucleotides that encode peptide RA1 as set forth in SEQ ID NO: 1 or fragments thereof such as those set forth in SEQ ID NOs: 2-34 as well as any derivative or analog thereof.

A polynucleotide of the present invention can be expressed as a secreted peptide where the peptide RA1, or a derivative, analog or fragment thereof is isolated from the medium in which the host cell containing the polynucleotide is grown, or the polynucleotide can be expressed as an intracellular peptide by deleting the leader or other peptides, in which case the peptide RA1, derivative, analog or fragment thereof is isolated from the host cells. The peptide RA1, derivative, analog or fragment thereof so isolated is then purified by standard protein purification methods known in the art.

The RA1 peptide, analogs, derivatives, or fragments thereof can also be provided to the tissue of interest by transferring an expression vector comprising an isolated polynucleotide encoding the RA1 peptide, an analog, derivative, or fragment thereof to cells associated with the tissue of interest. The cells produce the peptide such that it is suitably provided to the cells within the tissue to exert a biological activity such as, for example, to reduce or inhibit inflammatory processes or autoimmune response within the tissue of interest.

The expression vector according to the principles of the present invention further comprises a promoter. In the context of the present invention, the promoter must be able to drive the expression of the peptide within the cells. Many viral promoters are appropriate for use in such an expression vector (e.g., retroviral ITRs, LTRs, immediate early viral promoters (IEp) (such as herpes virus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the RA1 peptide, an analog, derivative or fragment thereof and the promoter are operably linked such that the promoter is able to drive the expression of the polynucleotide. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors are introduced into the cells in a manner such that they are capable of expressing the isolated polynucleotide encoding the RA1 peptide, a fragment, derivative or analog thereof contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772:95-104, the contents of which are hereby incorporated by reference in their entirety), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640, the contents of which are hereby incorporated by reference in their entirety), papilloma virus vectors, picornavirus vectors, polyoma virus vectors, retroviral vectors, SV40 viral vectors, vaccinia virus vectors, and other vectors. Additionally, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated polynucleotide are well known in the art (e.g., Sambrook et al., 1989, Molecular Cloning: A Laboratory Manual, 2d edition, Cold Spring Harbor Press, the contents of which are hereby incorporated by reference in their entirety) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising the polynucleotide of interest is introduced into the cells by any means appropriate for the transfer of DNA into cells. Many such methods are well known in the art (e.g., Sambrook et al., supra; see also Watson et al., 1992, Recombinant DNA, Chapter 12, 2d edition, Scientific American Books, the contents of which are hereby incorporated by reference in their entirety). Thus, in the case of prokaryotic cells, vector introduction can be accomplished, for example, by electroporation, transformation, transduction, conjugation, or mobilization. For eukaryotic cells, vectors can be introduced through the use of, for example, electroporation, transfection, infection, DNA coated microprojectiles, or protoplast fusion. Examples of eukaryotic cells into which the expression vector can be introduced include, but are not limited to, ovum, stem cells, blactocytes, and the like.

Cells into which the polynucleotide has been transferred under the control of an inducible promoter if necessary, can be used as transient transformants. Such cells themselves may then be transferred into a subject for therapeutic benefit therein. Thus, the cells can be transferred to a site in the subject such that the peptide of the invention is expressed therein and secreted therefrom and thus reduces or inhibits, for example, inflammatory processes so that the clinical condition of the subject is improved. Alternatively, particularly in the case of cells to which the vector has been added in vitro, the cells can first be subjected to several rounds of clonal selection (facilitated usually by the use of a selectable marker sequence in the vector) to select for stable transformants. Such stable transformants are then transferred to a subject, preferably a human, for therapeutic benefit therein.

Within the cells, the polynucleotide encoding the RA1 peptide, an analog, derivative or fragment thereof is expressed, and optionally is secreted. Successful expression of the polynucleotide can be assessed using standard molecular biology techniques (e.g., Northern hybridization, Western blotting, immunoprecipitation, enzyme immunoassay, etc.).

The RA1 peptide, an analog, derivative or fragment thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

The present invention further provides antibodies against RA1 or an analog or fragment thereof, such as against RA10. The antibodies can be polyclonal or monoclonal antibodies capable of binding to RA1 or a fragment or analog thereof. The antibodies are useful for detecting RA1 or analogs or fragments thereof in sera or any biological fluid or tissue of a subject. As shown in Example 10 herein below, antibodies raised against RA10 detected RA10 in mice resistant to EAE, but did not detect measurable amounts of RA10 in mice susceptible to EAE. Thus, antibodies against RA1 or a fragment or analog thereof are useful for diagnosing susceptibility to multiple sclerosis or to any other autoimmune or inflammatory disease.

The present invention further discloses that Zea Mays (Zea Maize, corn) contains the amino acid sequence AEMID-LAAKLISEGRG (SEQ ID NO:24) at residues 204-219. The present invention encompasses the peptide of SEQ ID NO:24, or an analog or fragment thereof. Thus, according to the present invention, peptides having at least 70% homology to RA1 of SEQ ID NO:1 or a fragment thereof, alternatively at least 80% homology, 90%, 95%, or 99% homology to SEQ ID NO:1 or a fragment thereof are included within the present invention.

According to a further aspect, the present invention provides a method for manufacturing an extract from Oryza sativa Japonica Group, wherein the extract has a an amount of a peptide consisting of the amino acid sequence AEMID-LAAKMLSEGRG as set forth in SEQ ID NO:1, comprising the steps of Oryza sativa Japonica Group comprising the steps:
  (i) heating Oryza sativa Japonica Group in water for a first predetermined period of time;
  (ii) cooling the Oryza sativa Japonica Group of step (i);
  (iii) mixing the Oryza sativa Japonica Group of step (ii) with an acid for a second predetermined period of time;
  (iv) separating a non-soluble soluble fraction from a soluble fraction; and
  (v) collecting the soluble fraction.

According to some embodiments, cooling the Oryza sativa Japonica Group is performed to a temperature of about 20° C. to about 25° C. In some embodiment, the heating is conducted so as to reach the boiling of the water.

In an embodiment of the invention, the peptide is extracted from the rice grain. In another embodiment it may be extracted from the stem, the leave, the root or from a cell in the grain, stem, leave or root or any combination thereof.

By "an amount of a peptide" it is meant that the peptide is detectable by method known in the art such as LC/MS, ELISA or any other method of detection that is know to those skilled in the art.

According to further embodiments, the acid is sulfuric acid.

In some embodiments of the invention other acids such as hydrochloric or nitric acid and weaker acids such as acetic acid may also be used. Further can be used other extraction procedures such as alcoholic extractions and combination of thereof with acids.

According to an embodiment of the invention, the concentration of the acid is in the range of about 10 mM to about 200 mM. According to another embodiment the concentration is in the range of about 30 mM to about 100 mM. According to another embodiment the concentration is at about 50 mM.

According to still further embodiments, the pH of the soluble fraction is adjusted to a pH of about 6.5 to about 7.5. In an embodiment of the invention, the pH of the soluble fraction is of about 7.0. It is to be understood that the method can further comprise the following steps: incubating the soluble fraction at 4° C. for a predetermined period of time, separating a second non-soluble fraction from the soluble fraction, and collecting said soluble fraction.

By "about" it is meant ±10%.

By "a predetermined period of time" it is meant the time until the reaction is finalized. Usually this period of time last from 1-3 minutes to 5-10 hours. Determination of a period of time for each reaction is well within the capability of those skilled in the art.

The present invention thus encompasses acid-soluble factors prepared according to the method disclosed herein above and compositions comprising same.

In an embodiment of the invention, there is provided an extract from Oryza sativa Japonica Group, having an amount of a peptide consisting of the amino acid sequence AEMID-LAAKMLSEGRG as set forth in SEQ ID NO:1 or a fragment, analog, or derivative thereof, wherein the fragment, analog, or derivative comprises at least three contiguous amino acid residues of SEQ ID NO:1.

In another embodiment of the invention, the peptide consists of the amino acid sequence AEMIDLAAKMLSEGRG as set forth in SEQ ID NO:1.

The amount of the peptide in the extract is between 1 fg/g to 1 mg/g. In another embodiment of the invention, the amount of the peptide in the extract is between 1 pg/g to 1 mg/g. In another embodiment of the invention, the amount of the peptide in the extract is between 1 ng/g to 1 mg/g. In another embodiment of the invention, the amount of the peptide in the extract is between 1 µg/g to 1 mg/g.

In an embodiment of the invention, the extract is enriched by exogenous peptide comprising the amino acid sequence AEMIDLAAKMLSEGRG as set forth in SEQ ID NO:1 or a fragment, analog, or derivative thereof, wherein the fragment, analog, or derivative comprises at least three contiguous amino acid residues of SEQ ID NO:1 so as to provide a therapeutically effective amount. By a "therapeutically effective amount" it is meant, an amount that can prevent, ameliorate, treat or delay the onset of the diseases described in the application, and in particular multiple sclerosis.

The invention further includes a method for treating/preventing/ameliorating/delaying the onset of a disease or condition attributable to inflammation and/or autoimmunity and/or neuroinflammation comprising administering to the subject in need a therapeutically effective amount of the extracts described herein.

Compositions and Administration Routes

The present invention provides a pharmaceutical composition comprising as an active ingredient a therapeutically effective amount of a source of RA1, and a pharmaceutically acceptable carrier. The present invention further provides a dietary supplement comprising a source of RA1, particularly RA1 peptide or an analog, fragment, or derivative thereof.

The source of RA1 refers herein to RA1 peptide, derivative, analog or fragment thereof, to an isolated polynucleotide encoding the RA1 peptide, a derivative, analog or fragment thereof, to an expression vector comprising an isolated polynucleotide encoding the RA1 peptide, a derivative, analog or fragment thereof, or to cells transfected with the expression vector as described herein above.

The pharmaceutical compositions of the invention can be formulated in the form of a pharmaceutically acceptable salt of the peptides of the present invention or their analogs, derivatives or fragments thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The pharmaceutical compositions or the dietary supplements can take the form of solutions, suspensions, emulsions, tablets, or capsules. The pharmaceutical compositions can also take the form of powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of a source of RA1, preferably in a substantially purified form, together with a suitable amount of carrier so as to provide the form for proper administration to the subject.

The amount of a source of RA1, which will be effective in the treatment of a particular disorder or condition will depend on the nature of the disorder or condition and on the particular RA1 source, and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, a source of RA1 can be supplied in any manner suitable for the provision of the peptide to cells within the tissue of interest. Thus, for example, a composition containing a source of RA1 (i.e., the RA1 peptide, or derivative, analog or fragment thereof, or an isolated polynucleotide encoding the RA1 peptide, a derivative, analog or fragment thereof, or an expression vector comprising an isolated polynucleotide encoding the RA1 peptide, a derivative, analog or fragment thereof, or cells transfected with the expression vector as described herein above) can be introduced, for example, into the systemic circulation, which will distribute the source of RA1 to the tissue of interest. Alternatively, a composition containing a source of RA1 can be applied topically to the tissue of interest (e.g., injected, or pumped as a continuous infusion, or as a bolus within a tissue, applied to all or a portion of the surface of the skin, etc.).

The route of administration of the pharmaceutical composition will depend on the disease or condition to be treated. Suitable routes of administration include, but are not limited to, parenteral administration, e.g., intradermal, intravenous, intramuscular, intralesional, subcutaneous, intrathecal, intraperitoneal, and any other mode of administration as known in the art. Although the bioavailability of peptides administered by other routes can be lower than when administered via parenteral injection, by using appropriate formulations it is envisaged that it will be possible to administer the compositions of the invention via oral, transdermal, rectal, vaginal, topical, nasal, inhalation and ocular modes of treatment. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material. According to some preferred embodiments, administration can be by direct injection e.g., via a syringe, at the site of a damaged tissue.

For topical application, RA1 peptide, or a derivative, analog or fragment thereof can be combined with a pharmaceutically acceptable carrier so that an effective dosage is delivered, based on the desired activity. According to an exemplary embodiment, the peptide of the invention is applied to the skin for treatment of diseases such as psoriasis. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to the ingredients of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

The RA1 peptide derivative, analog or a fragment thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

In yet another embodiment, the compositions of the present invention can be placed on a stent.

Uses of RA1 Peptides

The present invention provides a method for preventing, ameliorating, delaying the onset or treating a disease or disorder attributable to inflammatory/neuroinflammatory processes in a subject. The present invention also provides a method for treating a disease or condition attributable to free radicals in a subject. The present invention further provides a method for treating autoimmune diseases and other imbalanced immune responses. The invention provides in one of its embodiments a method for preventing, ameliorating or treating or delaying the onset multiple sclerosis. As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation.

In treating or preventing the above diseases, the compounds of the invention are administered in a therapeutically effective amount. The therapeutically effective amount will vary depending on the particular compound used and the route of administration, as is known to those skilled in the art.

According to the principles of the present invention, the methods comprise the step of administering to a subject in need thereof a pharmaceutical composition comprising as an active ingredient a therapeutically effective amount of a RA1 source and a pharmaceutically acceptable carrier. Alternatively, the dietary supplement or the extract of the present invention is useful for treating, preventing, ameliorating or delaying the onset of a disease or disorder attributable to inflammatory/neuroinflammatory processes or for treating, preventing, ameliorating or delaying the onset a disease or condition attributable to free radicals or for treating, preventing, ameliorating or delaying the onset autoimmune diseases and imbalanced immune responses.

The RA1 source according to the present invention includes the RA1 peptide, or a derivative, analog or fragment thereof according to principles of the present invention; an isolated polynucleotide sequence encoding the RA1 peptide, or a derivative, analog or fragment thereof; an expression vector comprising the isolated polynucleotide sequence encoding the RA1 peptide, or a derivative, analog or fragment thereof; and a host cell transfected with the expression vector comprising the isolated polynucleotide sequence of the invention. According to some embodiments, the RA1 source is the RA1 peptide or an analog, derivative or fragment thereof. According to a certain exemplary embodiment, the peptide is RA1 peptide of SEQ ID NO:1.

A "therapeutically effective amount" of the RA1 source is that amount of the RA1 source which is sufficient to provide a beneficial effect to the subject to which the source is administered. More specifically, a therapeutically effective amount means an amount of the source effective to prevent, alleviate or ameliorate tissue damage or symptoms of a disease of the subject being treated.

As anti-inflammatory agents, the peptides of the invention are expected to be efficacious in all diseases, disorders, or conditions that involve inflammation or inflammatory activity. Therefore, this invention relates to the protective effect of the RA1 source against all disorders or diseases that are related to or involve inflammation.

In an embodiment of the invention, autoimmune diseases including, but not limited to, multiple sclerosis, arthritis including rheumatoid arthritis, asthma, chronic bronchitis, inflammatory bowel disease (Crohn's disease), psoriasis, sepsis, and systemic lupus erythematosus (SLE) may be treated by RA1 or fragment or derivative thereof.

In an embodiment of the invention, chronic neurological degenerative diseases and muscle degenerative diseases may be treated, ameliorated or prevented by RA1 or fragment or derivative thereof.

The degenerative diseases include, but are not limited to, multiple sclerosis, Alzheimer's disease, Parkinson's disease, myasthenia gravis, muscle dystrophy, and amyotrophic lateral sclerosis.

Inflammation is also associated with hypersensitivity. Hypersensitivity includes, but is not limited to, immediate hypersensitivity, antibody mediated hypersensitivity, immune complex mediated hypersensitivity, T lymphocyte mediated hypersensitivity and delayed type hypersensitivity.

Inflammation is also associated with an infectious disease. Infectious diseases that can be treated with the pharmaceutical compositions of the invention include, but are not limited to, viral diseases, bacterial diseases, protozoan diseases, parasitic diseases, fungal diseases, and mycoplasma diseases. Thus, the compositions comprising the RA1 source of the invention can be used as cosmetics to eliminate skin infections.

Inflammation can also be associated with transplantation of a graft, such as, for example, in conditions of graft rejection or graft-versus-host (GVH) disease.

Inflammation can also be associated with an allergic disease and with musculo-skeletal inflammation. The musculo-skeletal inflammation is selected from the group consisting of arthritis, muscle inflammation, myositis, a tendon inflammation, tendinitis, a ligament inflammation, a cartilage inflammation, a joint inflammation, a synovial inflammation, carpal tunnel syndrome and a bone inflammation.

The peptides of the invention are useful for protecting against or treating T and or B cell mediated disease. T cell mediated diseases include, but are not limited to, psoriasis; allergy; T cell lymphomas and other malignancies; graft versus host disease; prevention of transplant rejection; bronchitis; asthma; autoimmunity; sarcoidosis; bone marrow depression; bone marrow stimulation; sepsis; Parkinson's disease; skin disorders and irritation; arthritis; multiple sclerosis; neurodegenerative disorders (amyotrophic lateral sclerosis, chorea, Alzheimer disease); atherosclerosis; fibrosis; pain; chronic or acute inflammation.

The protective effect of the peptides of the invention can be achieved by prophylactic treatment. The protective effect can also be achieved by post-exposure treatment with the peptide. Similarly, the protective effect of the peptides is achieved against inflammatory processes as exemplified herein below.

The term "protecting" relate to reduction of degree of lesion or biological damage as measured by gross pathology or histopathological evaluation, subjective burning sensation or other accepted parameters for tissue damage, lesion, discomfort and pain.

The pharmaceutical compositions of the invention can be used for accelerated healing of or prevention of development of wounds including decubitus, ulcers (also induced by drugs), internal and external wounds, abscesses and various bleedings.

The pharmaceutical compositions of the invention are useful for treatment or protection against tissue damage including, but not limited to, neuronal, neurological, skin, hepatic, nephrologic, urologic, cardiac, pulmonary, gastrointestinal, lower and upper airways, visual, audiologic, spleen, bone, and muscle damage. Treatment or protection against tissue damage can be accomplished in the fetus, newborn, child, adolescent as well as in adults and old persons, whether the condition or disorder to be treated is spontaneous, of traumatic of traumatic etiology or as a congenital defect.

The peptides of the present invention exhibit anti-inflammatory activity and/or immunomodulatory activity. As used herein, the term "immunomodulation" or immunomodulatory activity" refers to an affect on the functioning of the immune system, and includes both the enhancement of an immune response as well as suppression of the immune response.

It will be understood that the pharmaceutical compositions of the present invention can comprise the RA1 peptide, or a derivative, analog or fragment thereof or any other source of RA1, or all possible combinations of two or more of these peptide derivatives, analogs, or fragments or other sources of RA1.

Inflammatory diseases can affect the central nervous system (brain and spinal cord). Some of the best characterized disorders are multiple sclerosis (MS) and various forms of meningitis and encephalitis. A common feature of these diseases is a disruption of the blood-brain barrier (BBB) followed by inflammatory perivascular infiltration and eventual demyelination and astrogliosis.

Determination of a therapeutically effective amount of a peptide is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the peptides of the invention can be formulated or administered together with additional active ingredients as required to treat the condition of the patient.

In another embodiment of the invention, as can be seen from Example 10, the level of RA1 or fragments thereof may be used in a method for detecting the susceptibility of an individual to develop disease or condition attributable to inflammation and/or autoimmunity and/or neuroinflammation. The method for detecting comprises the step of measuring the level of the amino acid sequence AEMIDLAAKML-SEGRG as set forth in SEQ ID NO: 1 or any fragments thereof in a blood sample from the individual, wherein if the level is higher than the level of a normal individual, the individual is at risk to develop disease or condition attributable to inflammation and/or autoimmunity and/or neuroinflammation. The disease or condition attributable to inflammation and/or autoimmunity and/or neuroinflammation is multiple sclerosis.

By a "normal individual" it is meant an average level of some healthy individuals, that do not show clinical symptoms of the disease, which serves as a control. The level of the peptides in healthy individuals as opposed to ill individuals, can be determined by one skilled in the art by any assay using a capture molecule and a detector molecule to quantify captured molecules. Examples of immunoassays useful in the disclosure include, but are not limited to, radioimmunoassay (RIA), fluoroluminescence assay (FLA), chemiluminescence assay (CA), enzyme-linked immunosorbant assay (ELISA) and the like. The capture molecule can be in an embodiment of the invention, an antibody to amino acid sequence AEMID-LAAKMLSEGRG as set forth in SEQ ID NO: 1 or to any fragments thereof.

The invention further provides a kit to aid in diagnosis or prognosis of a disease condition by measuring the level of measuring the level of the amino acid sequence AEMID-LAAKMLSEGRG as set forth in SEQ ID NO: 1 in a blood sample comprising at least one capture molecule such as for example an antibody that specifically binds the amino acid sequence AEMIDLAAKMLSEGRG as set forth in SEQ ID NO: 1, and at least one detector molecule.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Effect of Sera of IIIM1-Treated Mice on Experimental Autoimmune Encephalitis

Female C57BL/6 Mice were i.v. injected with 1 mg/kg IIIM1 of the amino acid sequence KGHYAERVG as set forth in SEQ ID NO:31. Controls received saline injection. Three days later, sera of each group were obtained and injected iv into two groups of naive Female C57BL/6 mice (20-23 g) Thirty minutes later both groups (how many mice in each?) (n=13 for the peptide group and n=12 for the controls) were immunized with MOG using the following procedure:

Female C57BL/6 mice (20-23 g) were injected subcutaneously into four sites on the back, adjacent each of the forelimbs and hindlimbs (total volume 200 µl), with 200 µg myelin oligodendrocyte glycoprotein (MOG) 35-55 emulsified with 100 µl complete Freund's adjuvant, 800 µg *Mycobacterium tuberculosis* H37RA (Difco, Detroit, Mich.) and 80 µl phosphate buffered saline. Thereafter, each animal was injected intraperitoneally (i.p.) with pertussis toxin (PTX; 200 ng/mouse) and an additional PTX injection was repeated two days later.

The animals were evaluated for neurological score as follows: 0=normal; 0.5=mild ataxia of the hind limb; 1=decreased tail tone; 1.5=righting reflex within 3 sec; 2.0=righting reflex between 4-7 sec; 2.5—righting reflex between 7-10 sec; 3=hind limbs paralysis or absolute loss of righting reflex; 4=front and hind limbs paralysis; 5=moribund state; 6=death.

As can be seen in FIG. 1, sera from mice injected with IIIM1 significantly reduced the neurological symptoms associated with EAE in mice indicating for a serum factor induced by the IIIM1 that has beneficial effect on the EAE mice.

Example 2

Effect of Intravenous Injection of RA1 on EAE Model

Female C57BL/6 mice (20-23 g) were injected subcutaneously into four sites on the back, adjacent each of the forelimbs and hindlimbs (total volume 200 µl), with 200 µg myelin oligodendrocyte glycoprotein (MOG) 35-55 emulsified with 100 µl complete Freund's adjuvant, 800 µg *Mycobacterium tuberculosis* H37RA (Difco, Detroit, Mich.) and 80 µl phosphate buffered saline. Thereafter, each animal was i.p. injected with pertussis toxin (PTX; 200 ng/mouse) and an additional PTX injection was repeated two days later. RA1 dissolved in saline, was i.v. injected on the day of MOG immunization (n=10). Controls received saline injection (n=9). Neurological effects were scored and quantified.

Figure 2A:
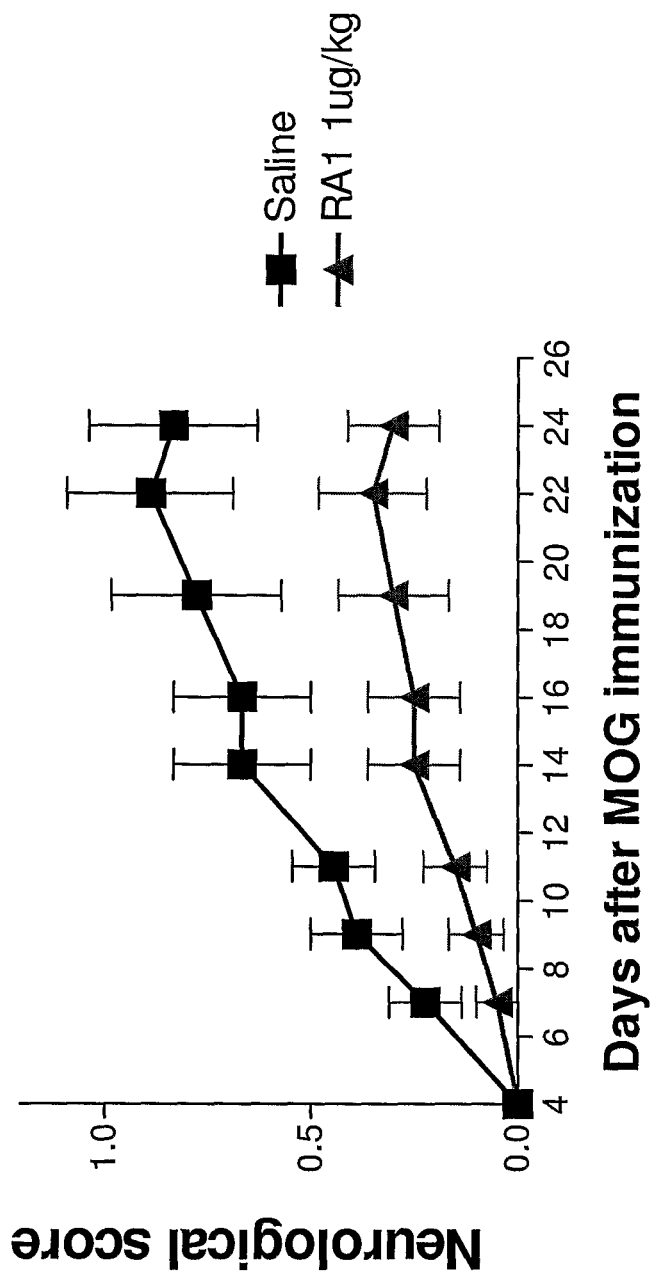
FIG. 2A shows the effect of intravenous (i.v.) injection of RA1 peptide on experimental autoimmune encephalitis (EAE) in mice. Female mice were subcutaneously (s.c) injected with MOG peptide 35-55 emulsified with complete Freund's adjuvant, *Mycobacterium tuberculosis* and phosphate buffered saline (PBS). Each animal was injected intraperitoneally (i.p.) with pertussis toxin and the injection was repeated after two days. The peptide, dissolved in saline, was administered i.v. once on the day of MOG immunization. The animals were evaluated for neurological score. Similar results were obtained with an i.p. injection of 1 μg/kg RA1 starting 7 days after MOG immunization, 3 times a week (FIG. 2B) Lastly, orally administered RA1 (100 μg/kg, 3 times a week, staring 7 days after MOG immunization) was also beneficial in reducing the neurological symptoms in EAE mice (FIG. 2C).
Figure 2B:
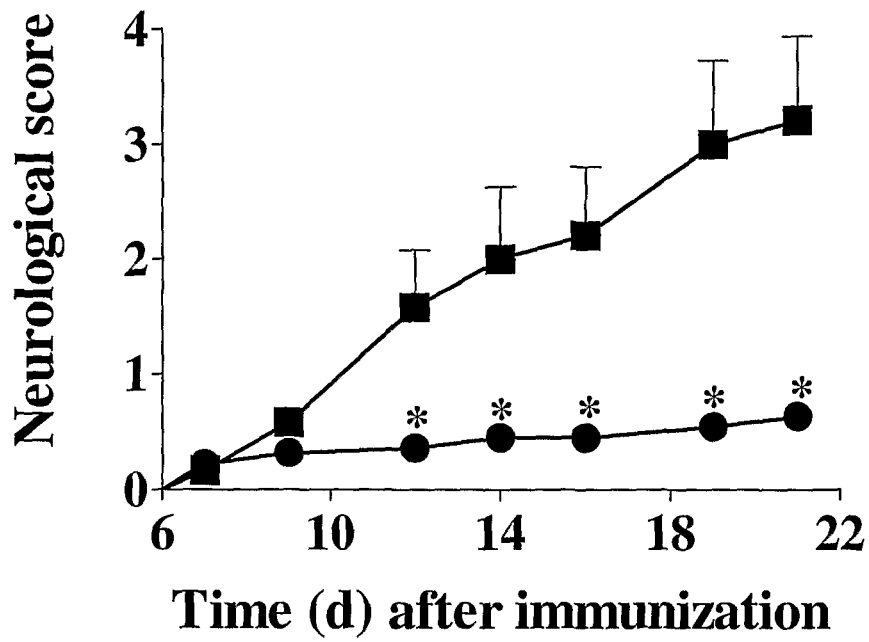
Figure 2C:
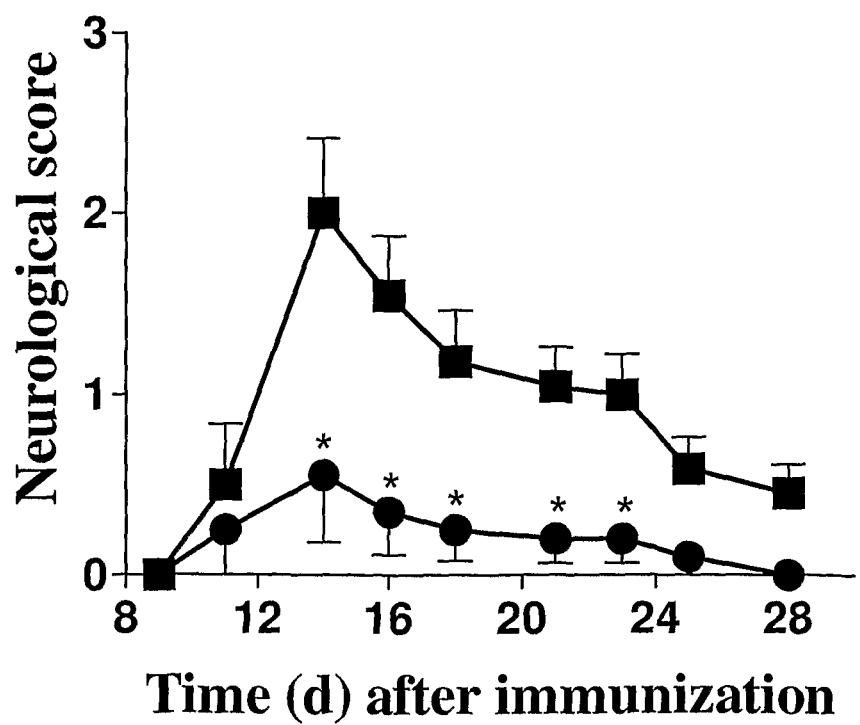

As can be seen in FIG. 2A the neurological score was significantly improved after i.v. administrations of RA1. Similar results were obtained with an i.p. injection of 1 µg/kg RA1 starting 7 days after MOG immunization and administered 3 times a week (FIG. 2B) Lastly, orally administered RA1 (100 µg/kg, 3 times a week, starting 7 days after Mog immunization) was also beneficial in reducing the neurological symptoms in EAE mice (FIG. 2C).

Example 3

Effect of RA1, RA3, RA4 on EAE in Mice

Female C57BL/6 mice (20-23 g) were immunized with myelin oligodendrocyte glycoprotein (MOG) peptide 35-55. Each mouse was sc injected into 4 sites on the back, adjacent to each of the forelimbs and hindlimbs (total volume 200 µl), with 200 µg MOG emulsified with 100 µl complete Freund's adjuvant (CFA, Difco, Detroit, Mich.), 800 µg *Mycobacterium tuberculosis* H37RA (Difco) and 80 µl phosphate buffered saline (PBS, Beit HaEmek, Israel). Each animal was ip injected with pertussis toxin (List Biological Laboratories Inc., CA) (200 ng/mouse) and the injection was repeated after 2 days. The peptide, (100 µg/kg, 3 times a week, starting 7 days after MOG immunization dissolved in saline, was administered as indicated. The animals were evaluated for neurological score as follows: 0=normal; 0.5=mild ataxia of the hind limb; 1=decreased tail tone; 1.5=righting reflex within 3 sec; 2.0=righting reflex between 4-7 sec; 2.5—righting reflex between 7-10 seconds; 3=hind limbs paralysis or absolute loss of righting reflex; 4=front and hind limbs paralysis; 5=moribund state; 6=death.

Figure 3:
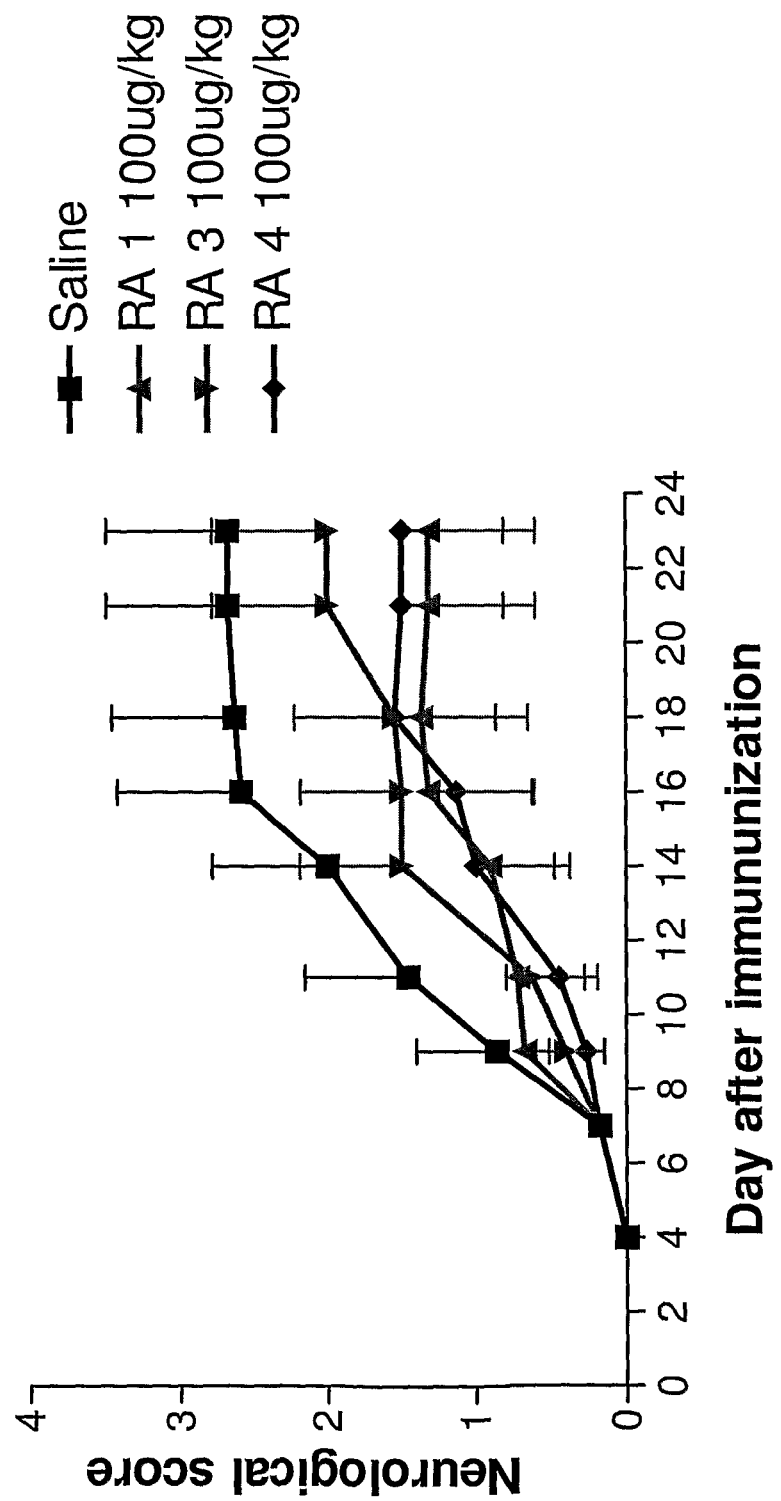
FIG. 3 shows the effect of oral administration of RA1, RA3, and RA4 on EAE in mice. Female mice were subcutaneously (s.c) injected with MOG peptide 35-55 emulsified with complete Freund's adjuvant, *Mycobacterium tuberculosis* and phosphate buffered saline (PBS). Each animal was injected intraperitoneally (i.p.) with pertussis toxin and the injection was repeated after two days. The peptide, dissolved in saline, was administered orally (po), three times a week, starting seven days after MOG immunization. The animals were evaluated for neurological score.

FIG. 3 shows the effect of RA1, RA3, and RA4 on EAE in mice. As can be seen, although RA3 and 4 (100.0 µg/kg) resulted in reduction of the neurological score in EAE mice, an increased effect was observed with RA1 at the same amount.

Example 4

Effect of RA1 and RA2 on EAE in Mice

Female C57BL/6 mice (20-23 g) were immunized with myelin oligodendrocyte glycoprotein (MOG) peptide 35-55. Each mouse was sc injected into 4 sites on the back, adjacent to each of the forelimbs and hindlimbs (total volume 200 µl), with 200 µg MOG emulsified with 100 µl complete Freund's adjuvant (CFA, Difco, Detroit, Mich.), 800 µg *Mycobacterium tuberculosis* H37RA (Difco) and 80 µl phosphate buffered saline (PBS, Beit HaEmek, Israel). Each animal was ip injected with pertussis toxin (List Biological Laboratories Inc., CA) (200 ng/mouse) and repeated after 2 d. The peptide, dissolved in saline, was administered as indicated. The animals were evaluated for neurological score as follows: 0=normal; 0.5=mild ataxia of the hind limb; 1=decreased tail tone; 1.5=righting reflex within 3 sec; 2.0=righting reflex between 4-7 sec; 2.5—righting reflex between 7-10 sec; 3=hind limbs paralysis or absolute loss of righting reflex; 4=front and hind limbs paralysis; 5=moribund state; 6=death.

Figure 4:
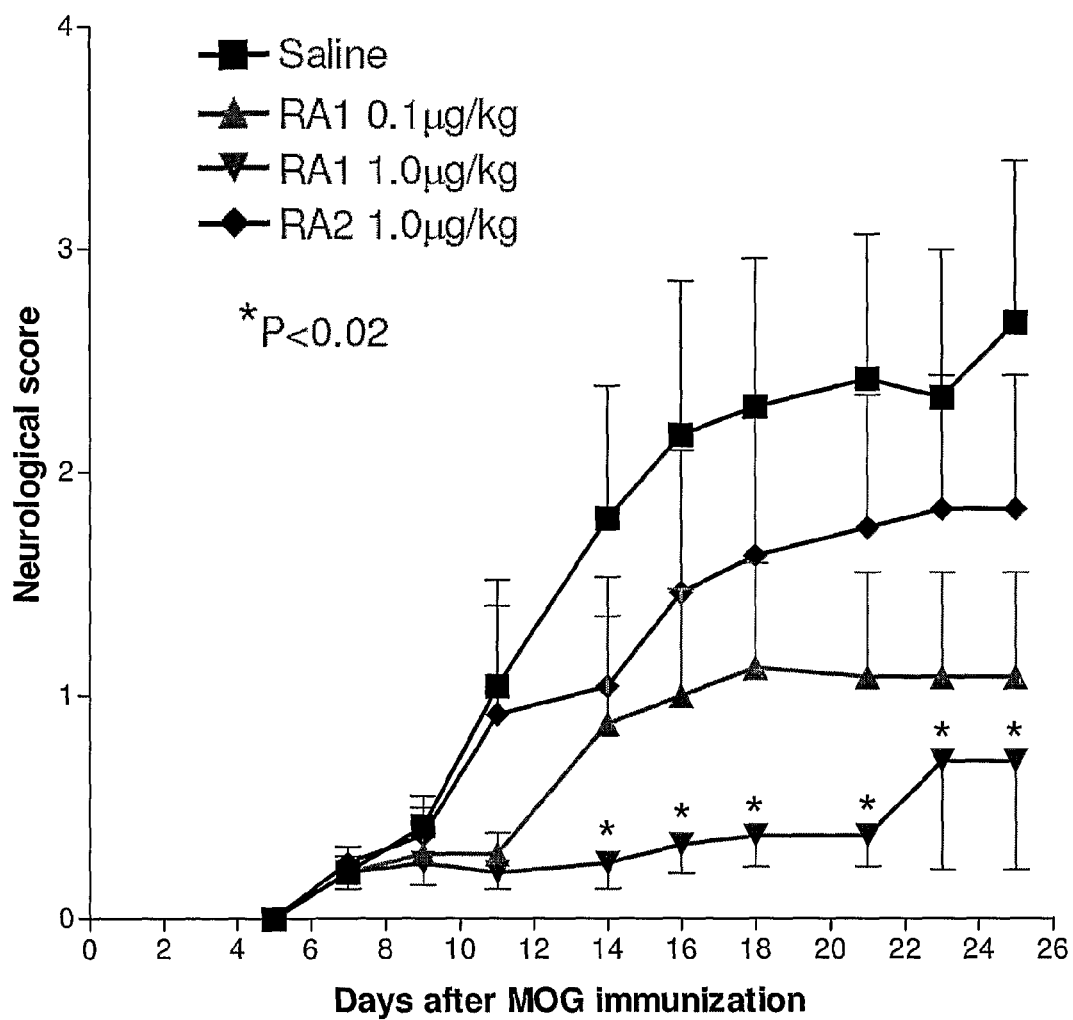
FIG. 4 shows the effect of intraperitoneal administration of RA1 and RA2 on EAE in mice. Female mice were subcutaneously (s.c) injected with MOG peptide 35-55 emulsified with complete Freund's adjuvant, *Mycobacterium tuberculosis* and phosphate buffered saline (PBS). Each animal was injected intraperitoneally (i.p.) with pertussis toxin and the injection was repeated after two days. The peptide, dissolved in saline, was injected i.p., three times a week, starting seven days after MOG immunization. The animals were evaluated for neurological score.

FIG. 4 shows the effect of RA1 and RA2 on EAE mice. As can be seen, although RA2 (1.0 μg/kg) resulted in reduction of the neurological score in EAE mice, an increased effect was observed with RA1 at a lower amount (0.1 μg/kg), whereas the effect of RA1 (1.0 μg/kg) on the neurological score was much more considerable (the score was less than 0.5).

Example 5

Effect of RA1 on Carrageenan-Induced Hind Paw Swelling

The effect of RA1 was tested in an animal model for inflammation. Inflammation induced by carrageenan, is acute, well-researched, and highly reproducible. Cardinal signs of inflammation edema, hyperalgesia, and erythema develop immediately following subcutaneous injection, resulting from action of proinflammatory agents bradykinin, histamine, tachykinins, complement and reactive oxygen, and nitrogen species. The inflammatory response is usually quantified by increase in paw size (edema).

RA1 or its vehicle, i.e., saline, was injected ip 30 minutes prior to carrageenan treatment. Carrageenan (50 μl of 3 mg/ml) was injected into the subplantar area of both limbs of each animal. The diameter of the subplantar area was measured every 60 minutes by a micrometer. The degree of swelling was assessed by the difference between thicknesses measured after and prior to carrageenan injection (zero time). The anti-inflammatory effect of RA1 is demonstrated.

Figure 5:
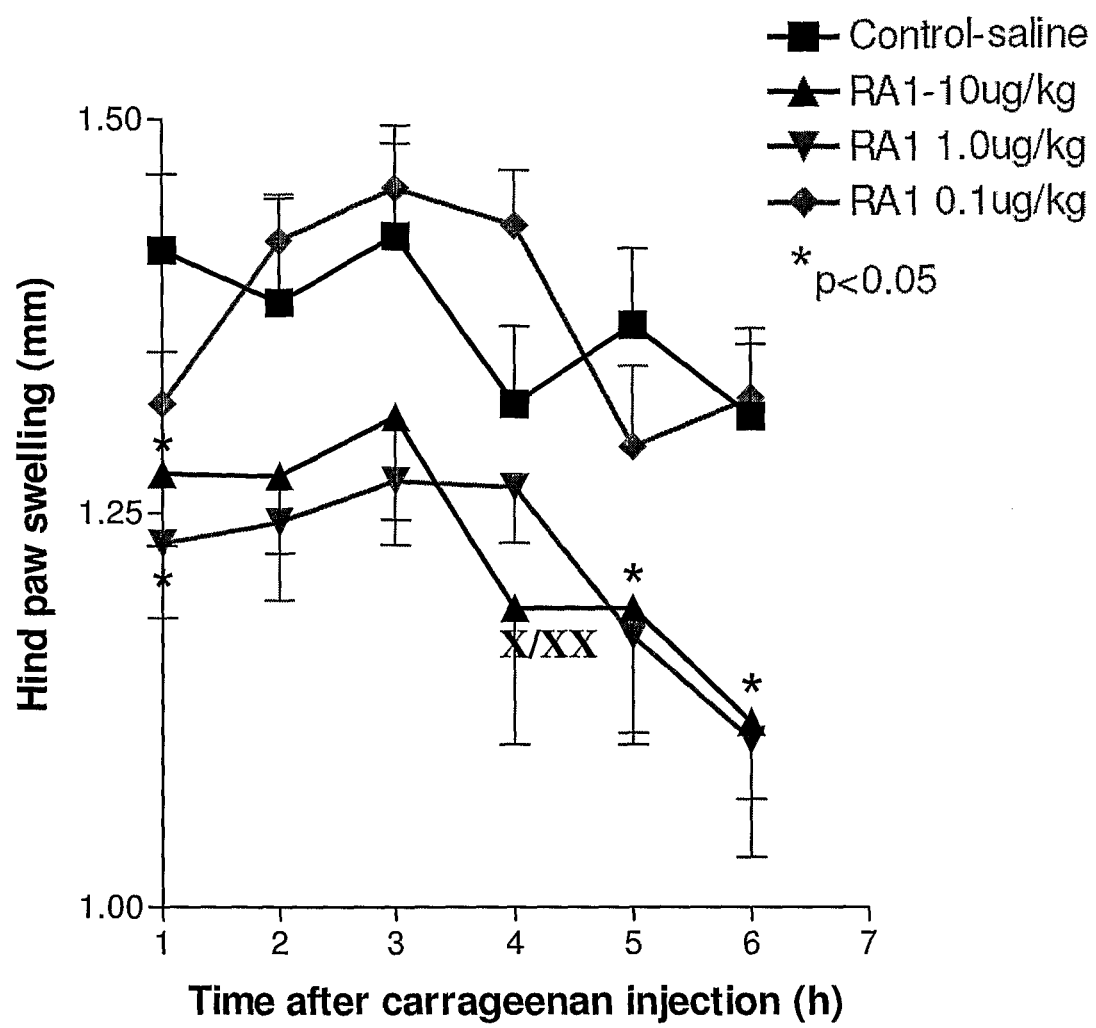
FIG. 5 shows the effect of RA1 on carrageenan-induced hind paw swelling. RA1 or saline were injected 30 minutes prior to carrageenan injection into the subplantar area. The diameter of the subplantar area was measured every 60 minutes by a micrometer. The degree of swelling was assessed by the difference between thicknesses measured after and prior anti-inflammatory effect of RA1 is demonstrated.

FIG. 5 shows the effect of RA1 on carrageenan-induced hind paw swelling. As can be seen, the swelling induced after the carrageenan injection was significantly reduced by one dose of RA1 1.0 μg/kg and 10 μg/kg injected prior to the carrageenan injection.

Example 6

The Effect of RA1 on Oxidative Burst of Mouse Peritoneal Macrophages

Mice were injected ip with 1.5 ml thioglycolate (29.8 g/l). Peritoneal macrophages were obtained and incubated (2.5× $10^6$ cells/ml) in HBSS with 2 μl of 1 mM $CoCl_2$, 2 μl 100 mM $Na_2SeO_3$, 2 μl of 10 mM luminal. The reaction started by the addition of 5 μl of 100 μM phorbol myristate acetate (PMA) (final concentration of 2.5 μM) and one minute later RA1 was added. Luminescence measurement was started after PMA addition. Each cycle represents 74 seconds.

Figure 6:
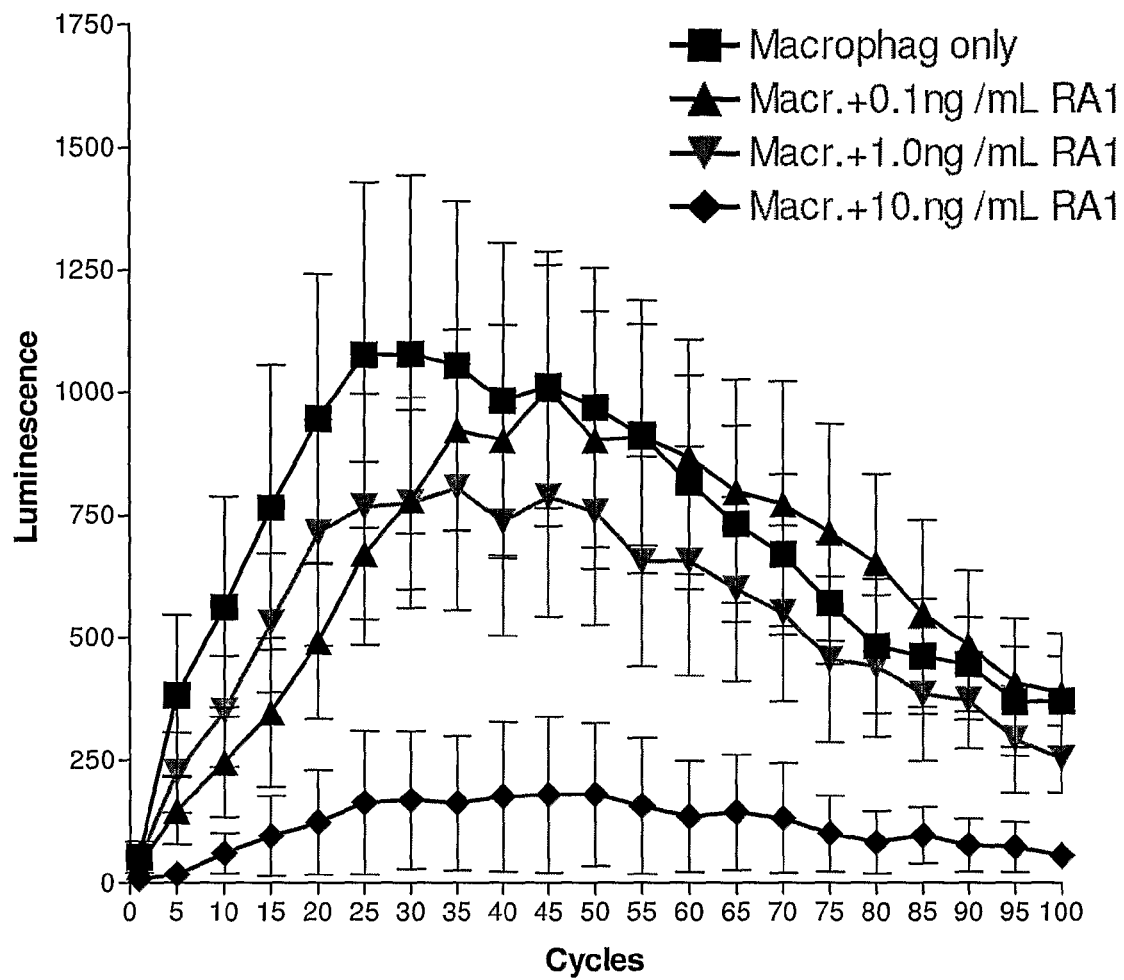
FIG. 6 shows the effect of RA1 on oxidative burst of mouse peritoneal macrophages. Mice were injected i.p. with thioglycolate. Peritoneal macrophages were obtained and incubated with horse-reddish peroxidase and luminol. The reaction started by the addition of phorbol myristate acetate (PMA) and 1 minute later RA1 was added. Luminescence measurement was started after PMA addition. Each cycle represents 74 seconds.

FIG. 6 shows the effect of RA1 on oxidative burst of mouse peritoneal macrophages. As can be seen, 10 ng/ml of RA1 strongly inhibited oxidatve burst in activated macrophages as measured by luminescence measurement after PMA addition. Other concentrations of RA1 (0.1 ng/ml and 1.0 ng/ml) were less effective.

Example 7

The Effect of Oryza sativa Japonica Group Extract on EAE in Mice

The active EAE model was performed as described herein above.

Preparation of Oryza Sativa Japonica (R.J.) was carried out as follows: R.J. (4 g) washed in water was incubated in 8 ml water at room temperature for one hour ("with preincubation" while "without preincubation" means that this step was not performed) followed by boiling for 15 minutes until no water left. After cooling to room temperature, sulfuric acid (27 ml, 50 mM) was added and the mixture was stirred for 4 h. After centrifugation (20 minutes, 9,000 g) the supernatant was adjusted to pH 7.0 with NaOH and kept at 4° C. over night. The solution was re-centrifuged and the supernatant was re-adjusted to pH 7.0 when necessary.

Figure 7:
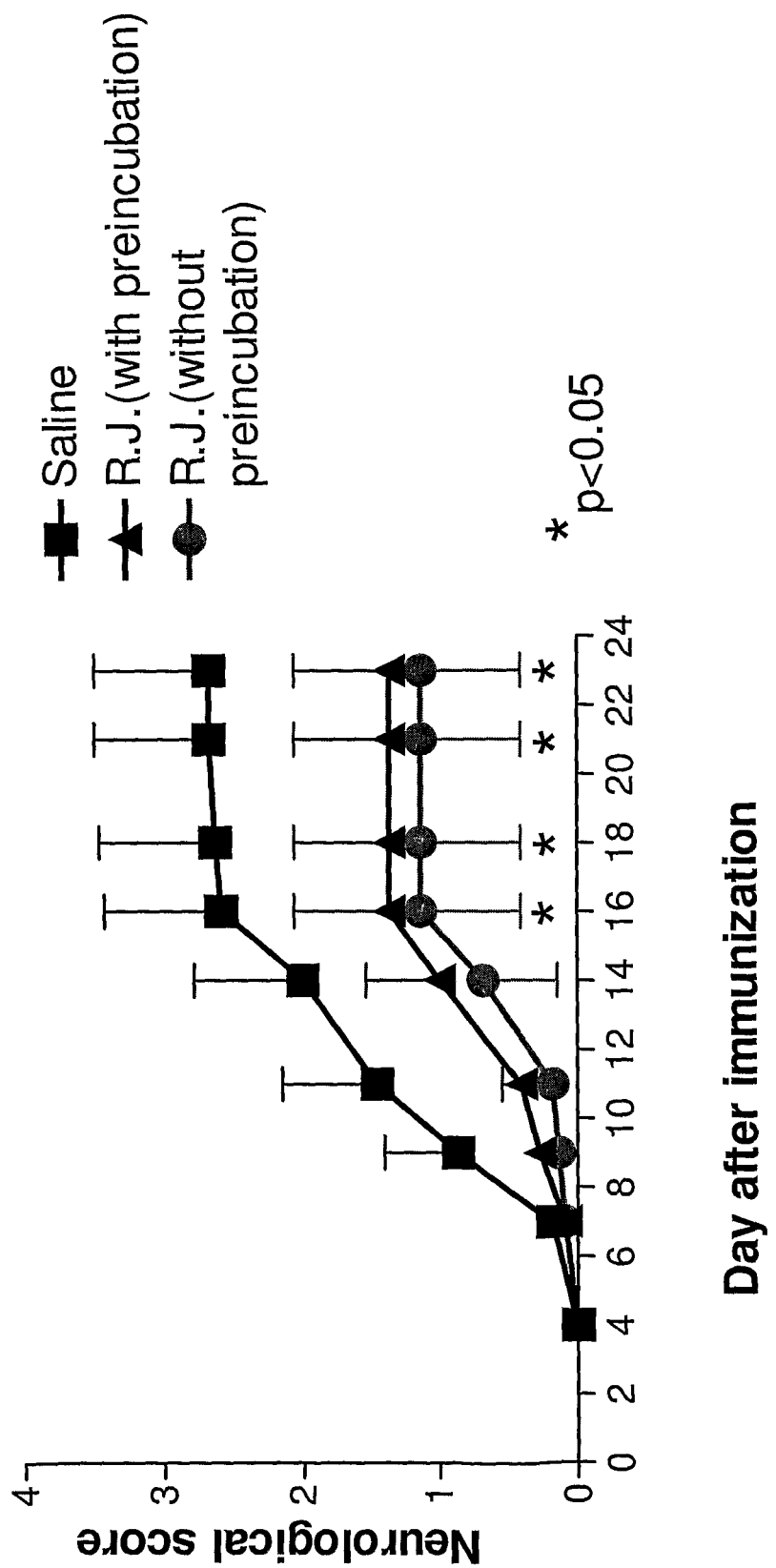
FIG. 7 shows the effect of oral administration of acid-soluble factors obtained from *Oryza Sativa* Japonica (RJ) on EAE in mice. RJ washed in water was incubated in water at room temperature for one hour ("with preincubation", while "without preincubation" means that this step was not performed) followed by boiling for 15 minutes until no water left. After cooling to room temperature, sulfuric acid was added and the mixture was stirred for four hours. After centrifugation (20 minutes, 9,000 g), the supernatant was adjusted to pH 7.0 with and kept at 4° C. over night. The solution was re-centrifuged and the pH of the supernatant was adjusted to pH 7.0. RJ was administered orally to EAE-induced mice three times a week, starting five days after MOG immunization. The neurological score was evaluated.

FIG. 7 shows the effect of oral administration of R.J. extracted by acid with or without preincubation in water for one hour at room temperature on EAE mice. As shown, the step of preincubation with water at room temperature for one hour did not affect the desired activity of the extract as provided in the neurological score analysis in EAE mice.

Example 8

Effect of Acid-Soluble Factors Extracted from Oryza Sativa Japonica on EAE in Mice The active EAE model was performed as described herein above.

Preparation of R.J. was carried out as follows:

R.J. in W+acid: RJ (4 g) washed in water was incubated in 8 ml water at room temperature for 1 h followed by boiling for 15 min until no water left. After cooling to room temperature, sulfuric acid (27 ml, 50 mM) was added and the mixture was stirred for 4 h. After centrifugation (20 min, 9,000 g) the supernatant was adjusted to pH=7.0 with NaOH and kept at 4° C. over night. The solution was recentrifuged and supernatant was readjusted to pH=7.0 when necessary.

R.J. in W: The same procedure including all incubations but without acidification (water instead of acid).

R.J. in acid: The same procedure but without preincubation and boiling. Uncooked R.J. was incubated in sulfuric acid as described and the rest was carried out according to the previous procedure.

Figure 8:
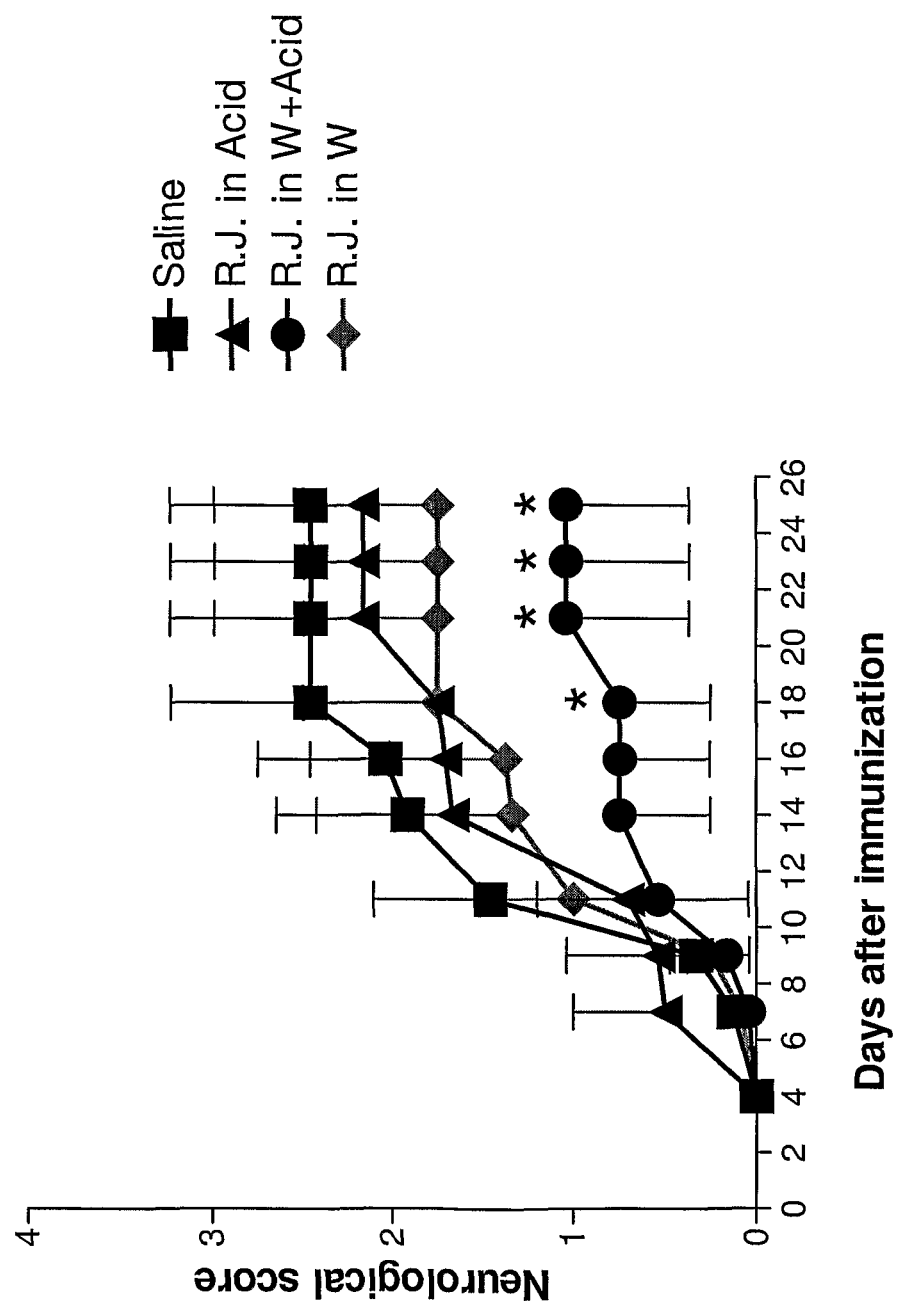
FIG. 8 shows the effect of oral administration of *Oryza Sativa* Japonica (RJ) on EAE mice. RJ was subjected to treatments in water (W), Acid, or water+acid (W+Acid), and then orally administered to mice immunized with MOG. The neurological score was evaluated.

FIG. 8 shows the effect of acid-soluble factors isolated from R.J. subjected to acid extraction on EAE in mice. Significant results were obtained when R.J was boiled in water and extracted with acid.

Example 9

Effect of RA5 on EAE in Mice

Female C57BL/6 mice (20-23 g) were immunized with myelin oligodendrocyte glycoprotein (MOG) peptide 35-55. Each mouse was injected (s.c.) into four sites on the back, adjacent to each of the forelimbs and hindlimbs (total volume 200 μl), with 200 μg MOG emulsified with 100 μl complete Freund's adjuvant (CFA, Difco, Detroit, Mich.), 800 μg Mycobacterium tuberculosis H37RA (Difco) and 80 μl phosphate buffered saline (PBS, Beit Haemek, Israel). Each animal was i.p. injected with pertussis toxin (List Biological Laboratories Inc., CA) (200 ng/mouse) and the injection was repeated after two days. The peptide, dissolved in dimethylsulfoxide and then diluted in saline, was orally (po) administered (100 μg/kg) starting five days after MOG administration and continued three times a week during the experiment. The animals were evaluated for neurological score as follows: 0=normal; 0.5=mild ataxia of the hind limb; 1=decreased tail tone; 1.5=righting reflex within 3 seconds; 2.0=righting reflex between 4-7 seconds; 2.5—righting reflex between 7-10 seconds; 3=hind limbs paralysis or absolute loss of righting reflex; 4=front and hind limbs paralysis; 5=moribund state; 6=death.

Figure 9:
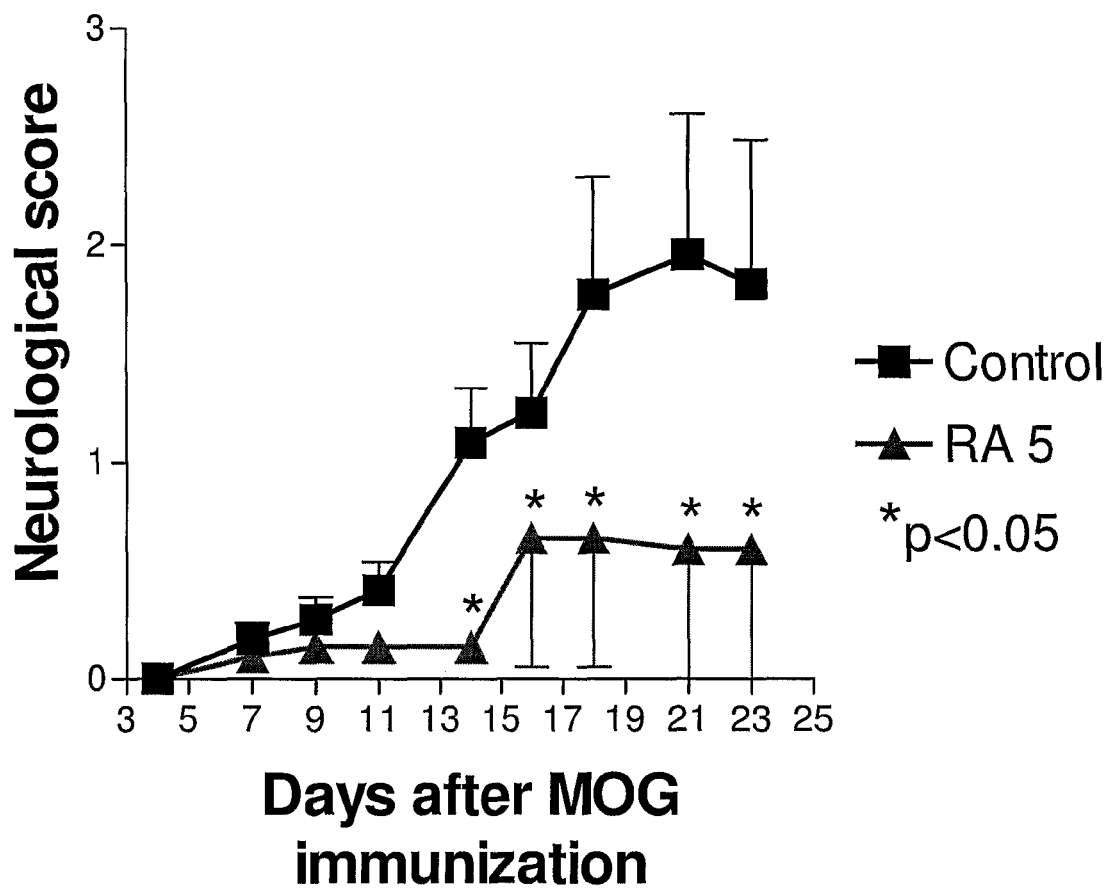
FIG. 9 shows the effect of oral administration of RA5 on EAE in mice. Female mice were subcutaneously (s.c) injected with MOG peptide 35-55 emulsified with complete Freund's adjuvant, *Mycobacterium tuberculosis* and phosphate buffered saline (PBS). Each animal was injected intraperitoneally (i.p.) with pertussis toxin and the injection was repeated after two days. The peptide, dissolved in saline, was administered orally (po), three times a week, starting five days after MOG immunization. The animals were evaluated for neurological score.

FIG. 9 shows the significant effect (P<0.05) of orally administered RA5 (AEMID as set forth in SEQ ID. NO. 2), 100 μg/kg, on the neurological score of EAE mice.

Example 10

RA1-Like Immunoreactivity in Sera

Polyclonal antibodies were raised against RA1. Detection of RA1 immunoreactivity showed that serum of BALB/C mice (resistant strain) contained 166 pg/ml RA1 (determined by ELISA) in comparison to undetectable amount in C57BL/6 mice (sensitive strain). The same trend was observed in spleen, namely, BALB/C mice contained 57 ng/g RA1 per wet weight whereas no peptide could be detected in C57BL/6 mice. The results indicate that serum determination of RA1 can be a predictor for susceptibility of individuals to MS and can be used as a diagnostic tool whereby patient can be well prepared to the coming illness.

Example 11

Cytokine Profile of RA1-Treated CD4 Cells

Murine lymph nodes and/or spleens were mashed, harvested and single cell suspension was passed through a 70 mm cell strainer and washed. Murine naïve CD4 cells were MACS separated using Miltenyi CD4 beads (Miltenyi Biotec GmbH, Bergisch Gladbach, ermany) according to manufacture instructions. Isolated T cells were seeded and activated with anti-CD3 (2 mg/ml) and anti-CD28 (5 mg/ml) (BD Biosciences, San Jose, Calif., USA) in the presence of IL2 (10 U/ml), (PeproTech Inc, Rocky Hill, N.J., USA). For cytokine production and RA1 determination supernatants were collected for ELISA. Cytokine analysis was performed in supernatants at 72 h using commercial kits: IFNγ, IL12 and IL4 (Perpotech), IL-17 (R&D systems) and IL10 (BD Biosciences).

Figure 10A:
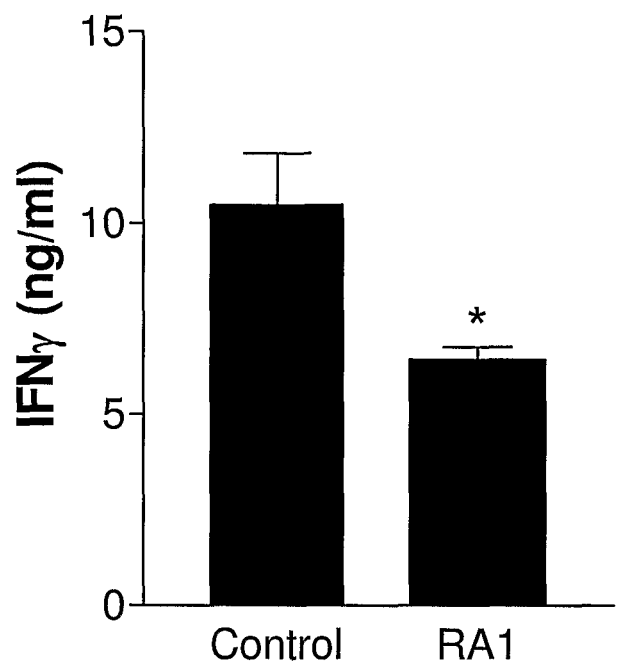
FIG. 10A-D shows the effect of RA1 on cytokine production by isolated naïve CD4 cells.
Figure 10B:
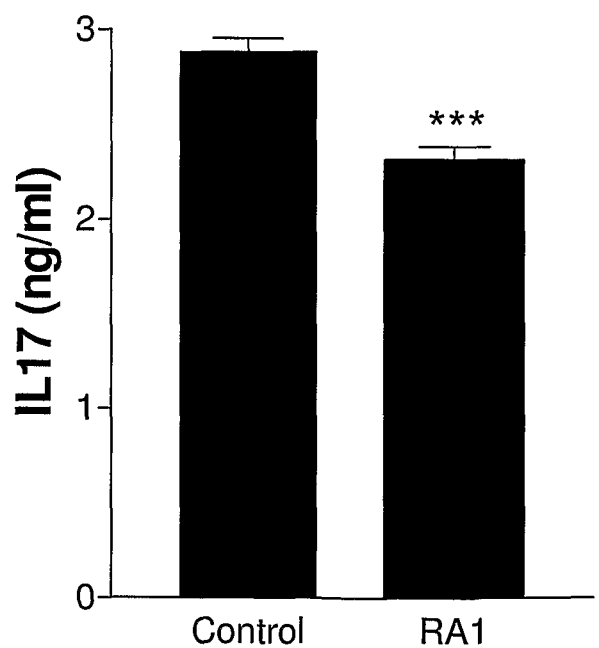
Figure 10C:
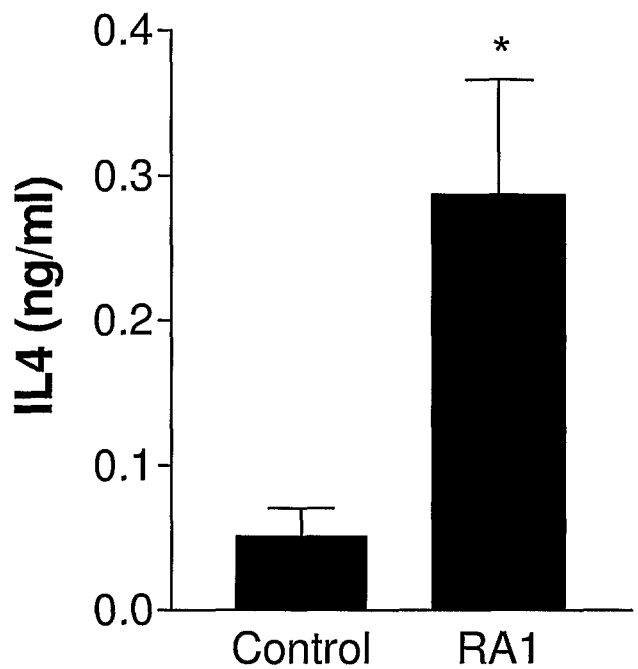
Figure 10D:
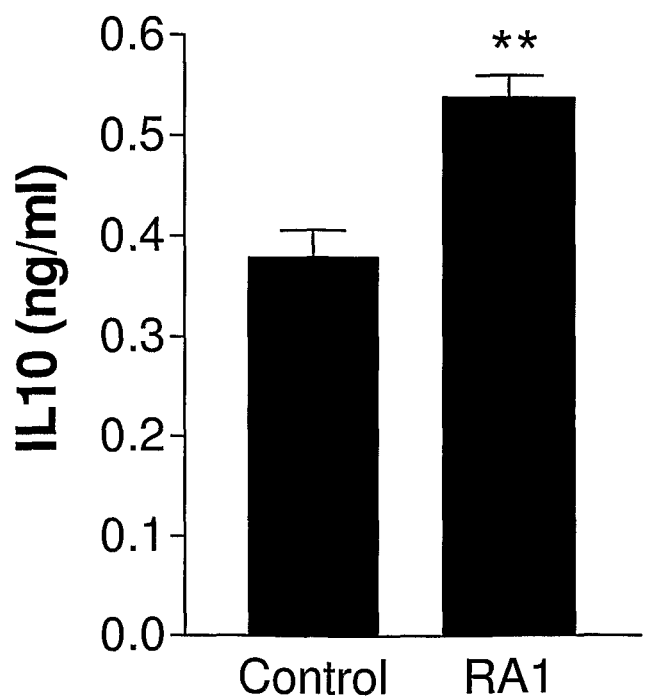

The cytokine profile of RA1-treated CD4 cells showed a reduction in IFNγ and IL17 (FIGS. 10A and 10B and elevation in IL4 and IL10 (FIGS. 10C and 10D).

It will be appreciated by persons skilled in the art that the present invention is not limited by what has been particularly shown and described herein above. Rather the scope of the invention is defined by the claims that follow.

---

The invention claimed is:

1. An isolated peptide consisting of an amino acid sequence AEMIDLAAKMLSEGRG as set forth in SEQ ID NO: 1.

2. A composition comprising an isolated peptide according to claim 1 and an acceptable carrier wherein said composition is a pharmaceutical composition, an extract, or a dietary supplement.

3. The composition of claim 2, wherein said extract is a composition comprising a peptide consisting essentially of the amino acid sequence AEMIDLAAKMLSEGRG as set forth in SEQ ID NO:1 derived from *Oryza sativa* Japonica Group.

4. The composition of claim 3, wherein the amount of said peptide is between 1 fg/g to 1 mg/g.

5. The composition of claim 3, wherein said extract is further enriched by an exogenous peptide comprising the amino acid sequence AEMIDLAAKMLSEGRG as set forth in SEQ ID NO:1.

* * * * *